US010000789B2

(12) United States Patent
Yang et al.

(10) Patent No.: US 10,000,789 B2
(45) Date of Patent: Jun. 19, 2018

(54) CELLULAR PROBE DEVICE, SYSTEM AND ANALYSIS METHOD

(71) Applicant: The Board of Regents of The University of Oklahoma, Norman, OK (US)

(72) Inventors: Zhibo Yang, Norman, OK (US); Renmeng Liu, Norman, OK (US); Ning Pan, Norman, OK (US); Wei Rao, Norman, OK (US); Rachel M. Vowcicefski, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days. days.

(21) Appl. No.: 14/967,071

(22) Filed: Dec. 11, 2015

(65) Prior Publication Data
US 2016/0168617 A1      Jun. 16, 2016

Related U.S. Application Data

(63) Continuation-in-part of application No. 14/742,485, filed on Jun. 17, 2015, now Pat. No. 9,595,428.
(Continued)

(51) Int. Cl.
*C12Q 1/24* (2006.01)
*H01J 49/16* (2006.01)
(Continued)

(52) U.S. Cl.
CPC .................. *C12Q 1/24* (2013.01); *G01N 1/02* (2013.01); *G01N 1/14* (2013.01); *H01J 49/0404* (2013.01);
(Continued)

(58) Field of Classification Search
CPC ... C12Q 1/24; G01N 1/02; G01N 1/14; G01N 1/04; G01N 2001/028; G01N 2001/149; H01J 49/0404; H01J 49/0004
(Continued)

(56) References Cited

U.S. PATENT DOCUMENTS 5,245,185 A     9/1993  Busch et al.
6,478,238 B1   11/2002  Wachs et al.
(Continued)

FOREIGN PATENT DOCUMENTS

WO        2001094931 A2     12/2001

OTHER PUBLICATIONS

Wachs, et al.; "Electrospray Device for Coupling Microscale Separations and Other Miniaturized Devices with Electrospray Mass Spectrometry"; Analytical Chemistry; vol. 73, No. 3, Feb. 1, 2001; pp. 632-638 (7 pages).
(Continued)

*Primary Examiner* — Nicole Ippolito
(74) *Attorney, Agent, or Firm* — Hall Estill Law Firm

(57) ABSTRACT

A sampling probe, system and analysis method is disclosed. The sampling probe in one embodiment is constructed of a silicon substrate having a first channel, a second channel, a first tapered tip with an opening, and a second tapered tip with an opening, wherein the first channel extends from the first tapered tip opening to the second tapered tip opening, and wherein the second channel extends from an inlet port to a junction with the first channel.

9 Claims, 17 Drawing Sheets

Related U.S. Application Data

(60) Provisional application No. 62/013,360, filed on Jun. 17, 2014, provisional application No. 62/090,739, filed on Dec. 11, 2014.

(51) Int. Cl.
| | |
|---|---|
| *G01N 1/14* | (2006.01) |
| *H01J 49/04* | (2006.01) |
| *G01N 1/02* | (2006.01) |
| G01N 1/04 | (2006.01) |
| H01J 49/00 | (2006.01) |

(52) U.S. Cl.
CPC .......... *G01N 1/04* (2013.01); *G01N 2001/028* (2013.01); *G01N 2001/149* (2013.01); *H01J 49/0004* (2013.01)

(58) Field of Classification Search
USPC ................................. 250/281, 282, 283, 288
See application file for complete search history.

(56) References Cited

U.S. PATENT DOCUMENTS

| | | | |
|---|---|---|---|
| 6,803,566 B2 | 10/2004 | Van Berkel | |
| 7,105,812 B2 | 9/2006 | Zhao et al. | |
| 8,110,797 B2 | 2/2012 | Marshall et al. | |
| 8,530,834 B2 | 9/2013 | Marshall et al. | |
| 9,595,428 B2* | 3/2017 | Yang ................... | H01J 49/0404 |
| 2004/0202994 A1* | 10/2004 | Timperman ........... | B01D 57/02 435/4 |
| 2006/0273808 A1 | 12/2006 | Van Berkel et al. | |
| 2012/0153143 A1 | 6/2012 | Kennedy et al. | |
| 2013/0341279 A1* | 12/2013 | Otsuka .................. | B01D 59/44 210/663 |
| 2014/0014747 A1 | 1/2014 | Moeller | |
| 2015/0158051 A1 | 6/2015 | Hoerr | |
| 2015/0364306 A1* | 12/2015 | Yang ................... | H01J 49/0404 250/282 |

OTHER PUBLICATIONS

Modestov, et al.; "Scanning Capillary Microscopy/Mass Spectrometry for Mapping Spatial Electrochemical Activity of Electrodes"; Analytical Chemistry; vol. 73, No. 17; Sep. 1, 2001; pp. 4229-4240 (12 pages).
Van Berkel; "Thin-Layer Chromatography and Electrospray Mass Spectrometry Coupled Using a Surface Sampling Probe"; Analytical Chemistry; vol. 74, No. 24, Dec. 12, 2002; pp. 6216-6223 (8 pages).
Gun, et al.; "Reduction of [(C5Me5)2Mo2O5] and [(C5Me5)2Mo2O4] in Methanol/Water/Trifluoroacetate Solutions Investigated by Combined On-Line Electrochemistry/Electrospray-Ionization Mass Spectrometry"; Eur. J. Inorg. Chem.; 2003; pp. 2264-2272 (9 pages).
Gun, et al.; "Studies on the Reduction of [(C5Me5)2Mo2O5] in Methanol/Water/Acetate Solutions by On-Line Electrochemical Flowcell and Electrospray Mass Spectrometry"; Eur. J. Inorg. Chem.; 2003; pp. 482-492 (11 pages).
Wachs, et al.; "A Device for Automated Direct Sampling and Quantitation from Solid-Phase Sorbent Extraction Cards by Electrospray Tandem Mass Spectrometry"; Analytical Chemistry; vol. 75, No. 7, Apr. 1, 2003; pp. 1769-1775 (7 pages).
Modestov, et al.; "On-line electrochemical-mass spectrometry study of the mechanism of oxidation of N,N dimethyl-p-phenylenediamine in aqueous electrolytes"; Journal of Electroanalytical Chemistry; vol. 565; 2004; pp. 7-19 (13 pages).
Modestov, et al.; "Radial Electrochemical Flow Cell for On-Line Coupling with Mass Spectrometry: Theory and Electrooxidation of Dimethylaminomethyl Ferrocene"; Electroanalysis; vol. 16, No. 5; 2004; pp. 367 378 (12 pages).
Ford, et al.; "An improved thin-layer chromatography/mass spectrometry coupling using a surface sampling probe electrospray ion trap system"; Rapid Communications in Mass Spectrometry; vol. 18; Apr. 14, 2004; pp. 1303-1309 (9 pages).
Asano, et al.; "Self-aspirating atmospheric pressure chemical ionization source for direct sampling of analytes on surfaces and in liquid solutions"; Rapid Communications in Mass Spectrometry; vol. 19; Jun. 26, 2005; pp. 2305-2312 (8 pages).
Ford, et al.; "Quantitative Thin-Layer Chromatography/Mass Spectrometry Analysis of Caffeine Using a Surface Sampling Probe Electrospray Ionization Tandem Mass Spectrometry System"; Analytical Chemistry; vol. 77, No. 14; Jul. 15, 2005; pp. 4385-4389 (5 pages).
Ford, et al.; "Thin-layer chromatography/electrospray ionization triple-quadrupole linear trap mass spectrometry system: analysis of rhodamine dyes separated on reversed-phase C8 plates"; Journal of Mass Spectrometry; vol. 40; Jul. 15, 2005; pp. 866-875 (10 pages).
Kertesz, et al.; "Automation of a Surface Sampling Probe/Electrospray Mass Spectrometry System"; Analytical Chemistry; vol. 77, No. 22; Nov. 15, 2005; pp. 7183-7189 (7 pages).
Van Berkel, et al.; "Evaluation of a surface-sampling probe electrospray mass spectrometry system for the analysis of surface-deposited and affinity-captured proteins"; Rapid Communications in Mass Spectrometry; vol. 20; Feb. 10, 2006; pp. 1144-1152 (9 pages).
Kelly, et al.; "Chemically Etched Open Tubular and Monolithic Emitters for Nanoelectrospray Ionization Mass Spectrometry"; Analytical Chemistry; vol. 78, No. 22; Nov. 15, 2006; pp. 7796-7801 (6 pages).
Roach, et al.; "Nonspray desorption electrospray ionization: an ambient method for liquid-extraction surface sampling in mass spectrometry"; Analyst, The Royal Society of Chemistry; vol. 135; Sep. 2010; pp. 2233-2236 (5 pages).
Laskin, et al.; "Tissue Imaging Using Nanospray Desorption Electrospray Ionization Mass Spectrometry"; Analytical Chemistry; vol. 84, No. 1; Jan. 3, 2012; pp. 141-148 (15 pages).
Tsuyama, et al.; "Molecular and Functional Analysis of Cellular Phenomena Using Single-Cell Mass Spectrometry"; Biol. Pharm. Bull.; vol. 35, No. 9; Sep. 2012; pp. 1425-1431 (7 pages).
Lanekoff, et al.; "Spatially resolved analysis of glycolipids and metabolites in living *Synechococcus* sp. PCC 7002 using nanospray desorption electrospray ionization"; Analyst, The Royal Society of Chemistry; vol. 138; Apr. 7, 2013; pp. 1971-1978 (9 pages).
Pan, Ning, et al.; "Single-probe Mass Spectrometry for Single Cell Analysis : Development and Applications"; Department of Chemistry and Biochemistry; University of Oklahoma; Conference on Ion Chemistry and Mass Spectrometry; Jan. 18, 2014; 16 pages.
Pan, Ning, et al.; Single-probe Mass Spectrometry: a Novel Method for Single Cell Analysis; Department of Chemistry and Biochemistry; University of Oklahoma; American Society for Mass Spectrometry; Jun. 18, 2014; 16 pages.
Pan, Ning, et al.; "Single-Probe: A Novel Sampling and Ionization Device for Mass Spectrometry Studies of Single Cells, Biological Tissues, and Sulfated Biomolecules"; Department of Chemistry and Biochemistry; University of Oklahoma; American Society for Mass Spectrometry; Jun. 18, 2014; 1 page.
Rao, Wei, et al.; "High resolution ambient MS imaging of mouse tissue by surface micro-extraction using the Single-probe"; Department of Chemistry and Biochemistry; University of Oklahoma; American Society for Mass Spectrometry; Jun. 18, 2014; 1 page.
Vowcicefski, Rachel, et al.; "Novel Ionization Method of Sulfated Peptides Using the Single-Probe Ionization Source"; Department of Chemistry and Biochemistry; University of Oklahoma; American Society for Mass Spectrometry; Jun. 18, 2014; 1 page.
Pan, Ning, et al.; "The Single-Probe: A Minitiarized Multifunctional Device for Single Cell Mass Spectrometry Analysis"; Anal. Chem.; vol. 86; Sep. 15, 2014; 9376-9380 (5 pages).
Bonislawski, Adam; "University of Oklahoma Team Develops Device for Mass Spec Analysis of Living Single Cells"; ProteoMonitor / GenomeWeb; Oct. 10, 2014; 4 pages.

* cited by examiner

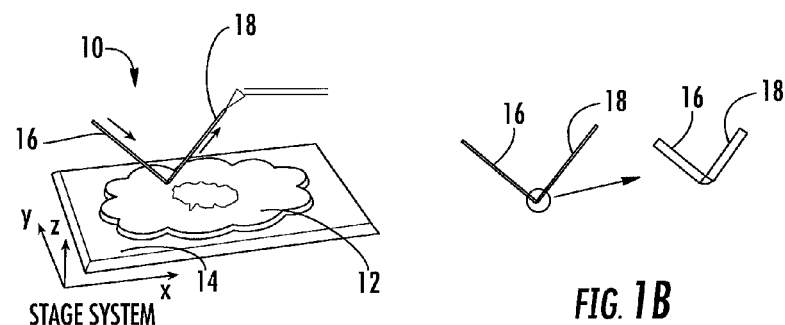
FIG. 1A
FIG. 1B
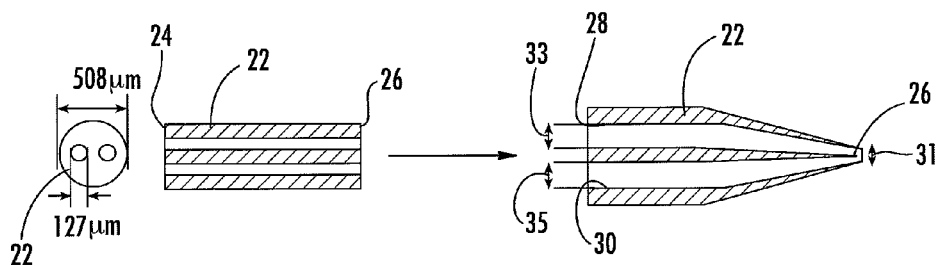
FIG. 2
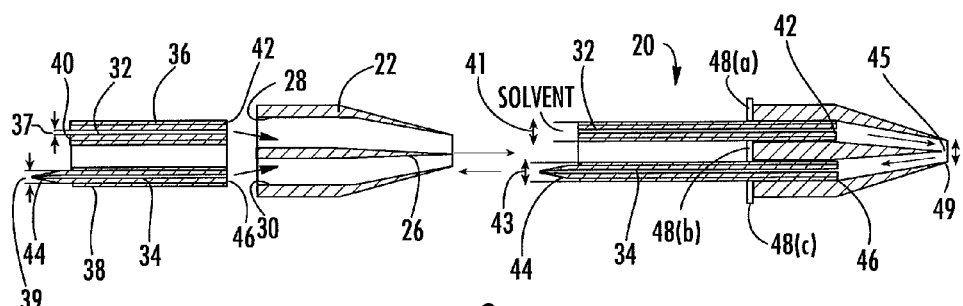
FIG. 3

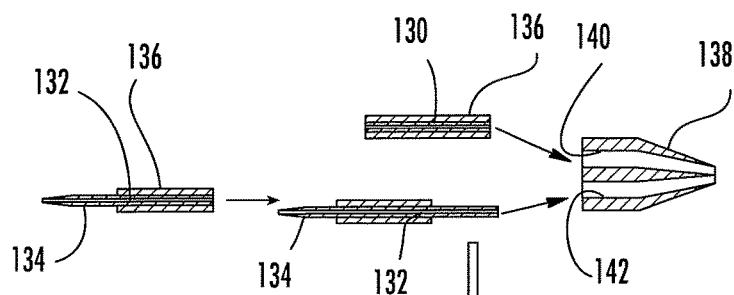
FIG. 12A
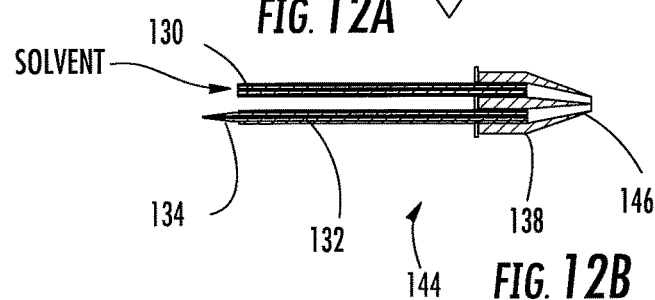
FIG. 12B
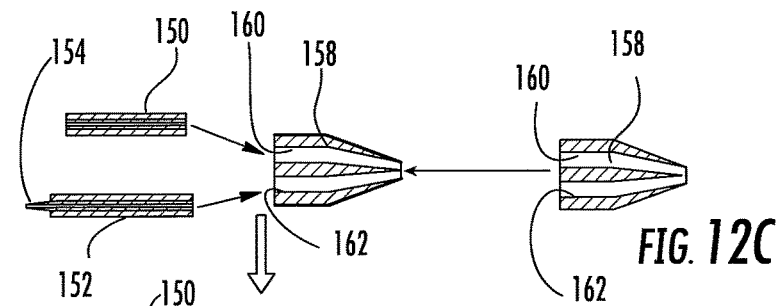
FIG. 12C
FIG. 12D
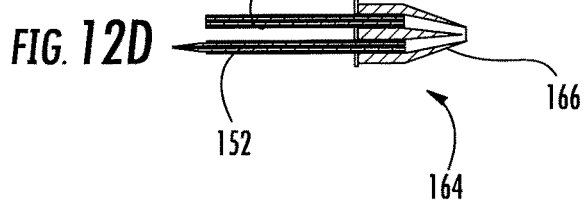
FIG. 12E
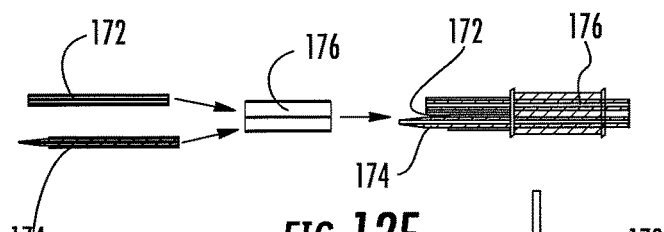
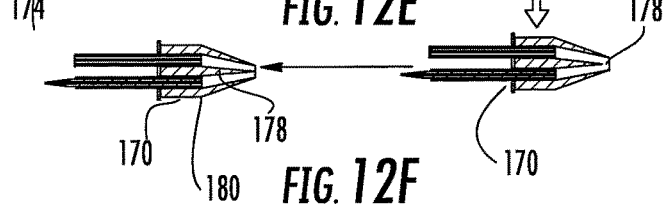
FIG. 12F

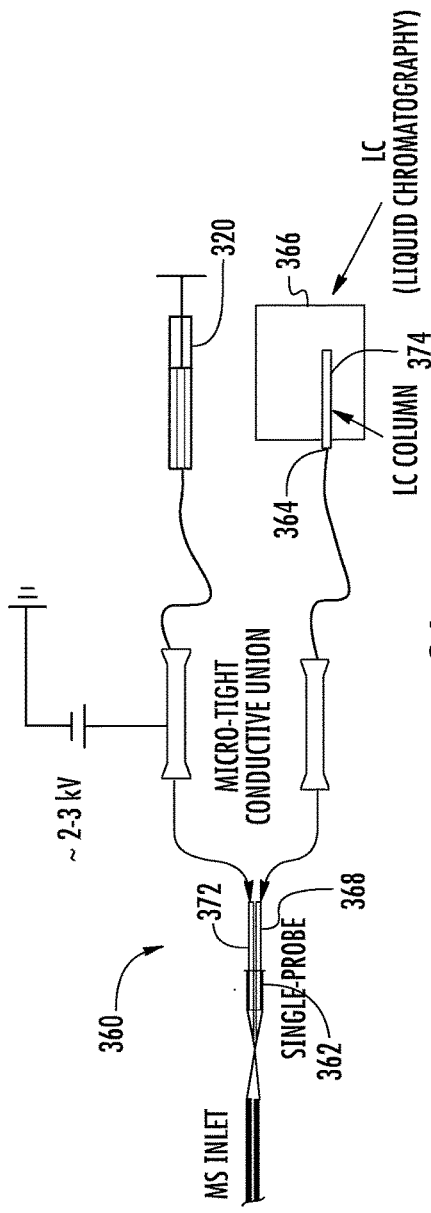
FIG. 24
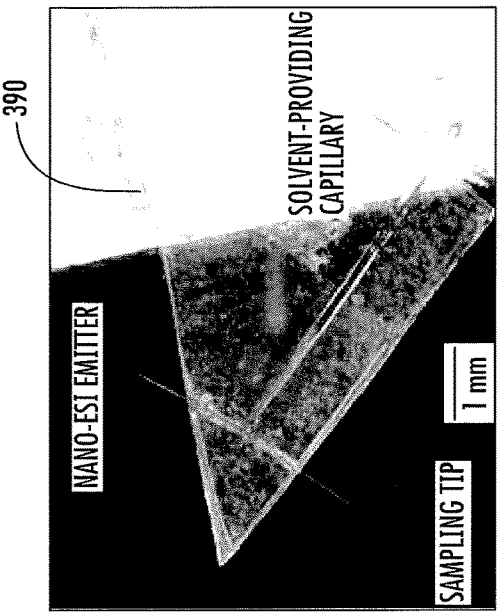
FIG. 25A
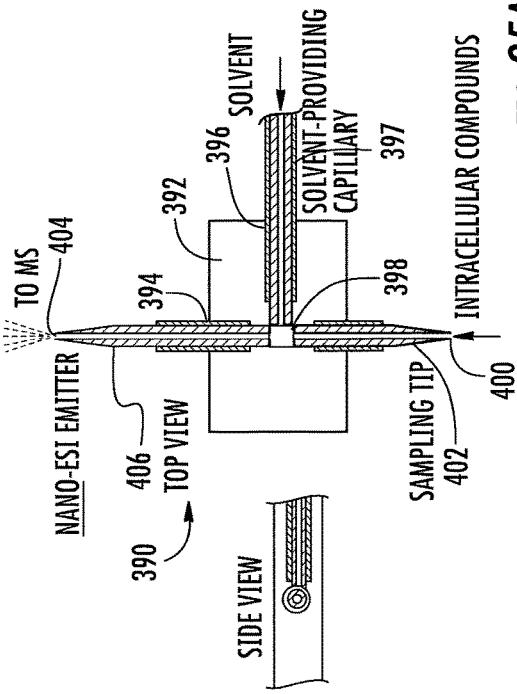

CELLULAR PROBE DEVICE, SYSTEM AND ANALYSIS METHOD

INCORPORATION BY REFERENCE STATEMENT

The present patent application claims priority to U.S. Provisional Patent Application U.S. Ser. No. 62/090,739, filed on Dec. 11, 2014. The present patent application also claims priority to U.S. patent application Ser. No. 14/742,485, filed Jun. 17, 2015, which claims priority to U.S. Provisional Patent Application U.S. Ser. No. 62/013,360 which was filed on Jun. 17, 2014. The entire contents of the referenced applications are hereby expressly incorporated herein by reference.

STATEMENT REGARDING FEDERALLY SPONSORED RESEARCH OR DEVELOPMENT

Not applicable.

BACKGROUND

Mass spectrometry imaging (MSI) is an emerging tool for mapping the spatial distribution of analytes in biological tissues at the molecular level. MSI has been successfully utilized to obtain rapid 2-D or 3-D spatial distributions of biological species (e.g., lipids, drugs and metabolites) present on different tissue slices (e.g., kidney, brain, liver, and tumor). This emerging scientific technology has the potential to reshape the analytical science of many research disciplines including human medicine, e.g., drug delivery and metabolomics, target cancer therapy, and cancer diagnosis.

A pivotal focus of MSI technique development is the improvement of the spatial resolution, and an ultimate goal in detection resolution is the ability to sample a single cell with mass spectrometry (MS). The ability to interrogate the molecular constituents of individual cells will be a major advancement in biological science. Currently and classically, molecular cell component analysis is almost exclusively done through lysate preparation of a cell population or a tissue sample, and all analysis represents an average of the disparate characteristics of the individual cells present; this limitation applies to common experimental analysis methods such as Western blotting and lipid analysis. Additionally, the preparation of a lysate or an extract from such a heterogeneous sample creates a completely ex vivo biological context—extremely disruptive reagents or processes rip apart the rigorous-spatially segregated cell, mixing all the constituents into a completely artificial milieu. This less-than-ideal experimental approach has been necessary due to the lack of analytical sampling sensitivity, and it is currently impossible to know how this deficient sample preparation system might have produced incorrect or biased results in countless experiments over the modern history of biological science. Single cell MS has the potential to completely change the paradigm of biological sampling for molecular analysis, and the impact of this technical advancement is impossible to underestimate.

Depending on the ionization environment, MSI can be generally classified into two major categories: (a) MSI under vacuum, such as secondary ion mass spectrometry (SIMS) and matrix-assisted laser desorption ionization (MALDI), and (b) ambient pressure MSI, such as desorption electrospray ionization (DESI), laser ablation electrospray ionization mass spectrometry (LAESI), and nanospray desorption electrospray ionization (nano-DESI). Although all above techniques, except for nano-DESI, have been commercialized, their applications are still limited by their drawbacks. Due to the difficulties to obtained high vacuum for samples containing water, the application of SIMS to biological systems has been greatly limited. In spite that MALDI has become the major technique for MIS, surface treatment is obligatory and very time-consuming. In addition, there are concerns regarding the influence of sample preparation on the spatial distribution of analytes. The development of ambient desorption/ionization techniques allows rapid imaging measurement without (or very little, if any) treatment of surfaces. However, these MSI techniques, including DESI, LAESI, and nano-DESI, have their own inherent shortcomings. For example, DESI has relatively low spatial resolution as well as issues of sensitivity, ionization efficiency, and tissue-specific ion suppression effects. LAESI is a destructive method, such that experiments are nearly non-reproducible. Nano-DESI is non-destructive and provides a high resolution, whereas the fabrication of the imaging probes and the operation of the device are challenging. Therefore, the development of new methods to improve existing MSI technique is urgently needed.

BRIEF DESCRIPTION OF THE DRAWINGS

Several embodiments of the presently disclosed inventive concepts are hereby illustrated in the appended drawings. It is to be noted however, that the appended drawings only illustrate several typical embodiments and are therefore not intended to be considered limiting of the scope of the presently disclosed inventive concepts. Further, in the appended drawings, like or identical reference numerals or letters may be used to identify common or similar elements and not all such elements may be so numbered. The figures are not necessarily to scale and certain features and certain views of the figures may be shown as exaggerated in scale or in schematic in the interest of clarity and conciseness. The bore dimensions shown in the figures are not limited to those shown therein and are only intended to be exemplary.

FIG. 1(a) depicts a conventional nano-DESI dual capillary imaging probing system and its use with a mass spectrometer to sample a tissue on an X-Y-Z movable stage system.

FIG. 1(b) is a close-up view of two capillaries of the system of FIG. 1.

FIG. 2 depicts in a sectional view one non-limiting embodiment of how a dual—bore tube can be pulled to form a narrow tip in one end.

FIG. 3 depicts in a sectional view how coated capillaries are inserted into a pulled dual-bore tube of FIG. 2 in accordance with one non-limiting embodiment of the present disclosure.

FIG. 12A-12F depicts capillaries and probes coated with Au (or other conductive material), 12A and 12B capillaries coated with a conductive material (e.g., gold) are inserted into a pulled dual-bore tube, 12C and 12D a pulled dual-bore tube is pulled then coated with a conductive material (e.g., gold) before insertion of the conductively-coated capillaries, 12E and 12F a Single-probe formed according to Example 3 is formed, then coated with a conductive material (e.g. gold).

FIG. 24 depicts an analysis system using the Single-probe to receive an analyte from a LC column for delivery to a MS inlet for analysis.

FIG. 25(a) depicts a probe embodiment (the T-probe) of the presently disclosed inventive concepts for use in single-cell analysis.

DETAILED DESCRIPTION

Figure 4:
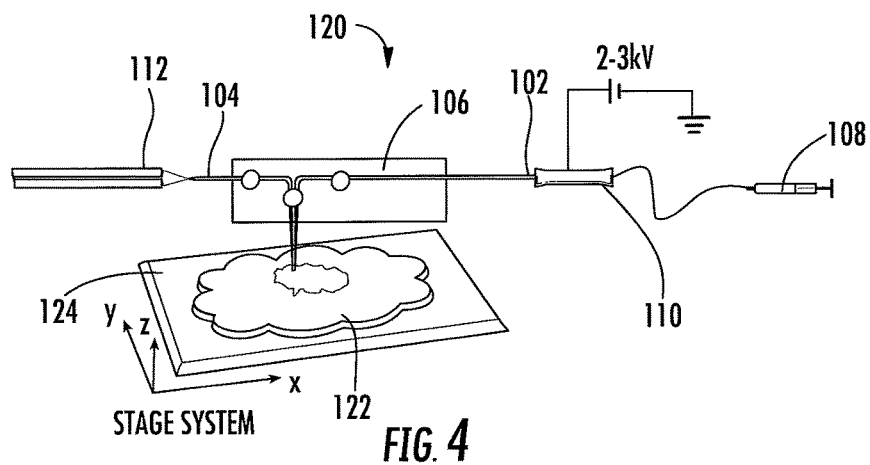
FIG. 4 depicts an experimental set up of a Single-probe MSI system of the present disclosure including a Single-probe, and a MS, and a solvent supplying device.

Before describing various embodiments of the present disclosure in more detail by way of exemplary description, examples, and results, it is to be understood that the present disclosure is not limited in application to the details of methods and compositions as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concept have been described in terms of particular embodiments, it will be apparent to those of skill in the art that variations may be applied to the compositions and/or methods and in the steps or in the sequence of steps of the method described herein without departing from the concept, spirit and scope of the inventive concepts. All such similar substitutes and modifications apparent to those of skill in the art are deemed to be within the spirit, scope and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. Further, in this detailed description and the appended claims, each numerical value (e.g., temperature or time) should be read once as modified by the term "about" (unless already expressly so modified), and then read again as not so modified unless otherwise indicated in context. Also, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

Where used herein the term "conductive material" includes any electrically-conductive material such as a metal, including but not limited to: gold, platinum, titanium; an inorganic, including but not limited to: diamond-like carbon and silicon monoxide; and a conductive polymer, including but not limited to polyaniline and a polypropylene/graphite mixture).

In at least one embodiment the present disclosure is directed to a new nano-DESI probe in which two fused capillaries (e.g., silica capillaries having outer diameter (OD)=150 µm and inner diameter (ID)=50 µm ID) are combined in a single unit to fabricate one sampling probe, the probe having a junction at the fused tips of the two capillaries. During a sampling measurement, a solvent (e.g., a methanol/water solution) is supplied through one capillary. The solvent dissolves the analytes on a small spot of the sample surface at the junction of the tips of the two capillaries. The solution containing the dissolved analytes is then collected at the tip of the second capillary and is transported through the second capillary to a narrowed orifice at an emitter end where the solution is ionized into charged droplets at an inlet of a mass spectrometer in a similar way of a conventional nano-spray ionization source. The ionized species in the solution are then analyzed the mass spectrometer, and m/z (mass/charge) information is collected and saved, e.g., by a computer. The sample slice can be placed on a motorized stage system, in which three stages can be independently controlled through a computer program, whereby the location information of analytes on the target spot can be recorded simultaneously along with their ion intensities. Eventually, the spatial distribution of molecules of interest can be mapped using visualization software by integrating information of both ion signal intensities and the corresponding coordinates.

Referring to FIGS. 1(a) and 1(b), a conventional nano-DESI dual capillary imaging probing system 10 is shown in use with a mass spectrometer (not shown) to sample a tissue 12 on an X-Y-Z movable system 14. A first capillary 16 for providing a charged solvent to the tissue and a second capillary 18 for receiving the analyte sampled by the mass spectrometer are utilized in the system 10. In conventional nano-DESI probe techniques (e.g., shown in FIG. 1) because two independent capillaries are needed to assemble the probe, systematic tests must be carried out to identify optimum parameters to determine the arrangement of the two capillaries, including the contact angle and distance, relative height, and profile of capillary orifice. Although adequate experience can be built up during the practice, it is still difficult to have a good quality control when fabricating a batch of such probes for series experiments. Due to these inherent drawbacks, fabricating prior nano-DESI probes has been very labor intensive and requires significant amount of experience. As a result this technique has not been widely adopted.

In the presently disclosed novel Single-probe the two capillaries have been integrated into an integral unit (the Single-probe) which can be directly coupled with a movable stage system and a MS for analysis of tissues and cells.

In certain embodiments, the Single-probe MSI of the present disclosure can be used to investigate the distribution of anti-cancer drugs (e.g., deguelin) in a variety of tissues (such as but not limited to, liver, kidney, brains, and breast cancer tumors) whereby 3-D images can be obtained by extrapolating 2-D images of a series of sections of an organ or a tumor.

EXAMPLES

The present disclosure, having now been generally described, will be more readily understood by reference to the following examples and embodiments, which are included merely for purposes of illustration of certain aspects and embodiments of the present disclosure, and are not intended to be limiting. The following detailed examples of methods of use and construction of the present disclosure and are to be construed, as noted above, only as illustrative, and not as limitations of the disclosure in any way whatsoever. Those skilled in the art will promptly recognize appropriate variations from the various structure, components, procedures and methods.

Example 1

As noted above, in at least one embodiment, the Single-probe device is constructed by incorporating at least two separate capillaries into a single integrated unit. Referring to FIG. 2-3, one non-limiting example of how a Single-probe 20 is constructed is described below: (1) Provide a dual-bore glass tube 22 having a first end 24 and a second end 26 (e.g., 508 μm OD, 127 μm ID, Friedrich & Dimmock, Inc.). Cut the dual-bore glass tube into ~5 cm long pieces, and pull a sharp tip on the second end 26 using a puller (not shown) (e.g., KOPF Vertical Pipette Puller, P-720) on the second end 26 (FIG. 2) so that the tube 22 is provided with a first bore 28 and a second bore 30. The tapered second end 26 of the tube 22 has an outer diameter 31 in a range of 0.1 μm to 50 μm. The first bore 28 and second bore 30 of the tube 22 have inner diameters 33 and 35 in a range of 1 μm to 500 μm.

(2) Provide a pair of fused silica capillary tubes 32 and 34 having outer polyimide coating material 36 and 38 (e.g., 150 μm OD, 50 μm ID, 5 cm long, PolyMicro Technologies). The tube 32 having a first end 40 and a second end 42. The tube 34 having a first end 44 and a second end 46. Remove the outer polyimide coating material 38 from an end 44 of one fused silica capillary 34 and pull the decoated end 44 into a sharp tip so that the decoated end 44 is sharp and narrowed and the other end 46 is blunt (FIG. 3). The first capillary 32 and second capillary 34 of the sampling probe 20 have inner diameters 37 and 39, respectively, in a range of 1 μm to 150 μm and outer diameters 41 and 43, respectively, in a range of 5 μm to 450 μm.

(3) Insert blunt ends 42 and 46 of the two capillaries 32 and 34 into the bores 28 and 30 of the pulled glass tubing 22 obtained from step 1, seal gaps 48(a)-48(c) using UV-light active epoxy (e.g., Prime Dent Light Cure Resin Dental Bonding Adhesive), and irradiate the entire piece with UV light for 30 seconds to form the integrated Single-probe 20 having a tip 49 (FIG. 3).

(4) The Single-probe 20 can then be used in conjunction with an MS apparatus as described in further detail below.

Example 2

As noted above, in at least one embodiment, the Single-probe device 20 is constructed by incorporating at least two separate capillaries into a single integrated unit. Another non-limiting example of how a Single-probe 50 is constructed is described below. Thus, the Single-probe 50 is constructed similar to the Single-probe 20 except as described herein:

(1) Provide a dual-bore glass tube 22 (e.g., 508 μm OD, 127 μm ID, Friedrich & Dimmock, Inc.). Cut the dual-bore glass tube 22 into ~5 cm long pieces, and pull a sharp tip using a puller (e.g., KOPF Vertical Pipette Puller, P-720) on one end 26 (as shown in FIG. 2).

Figure 5:
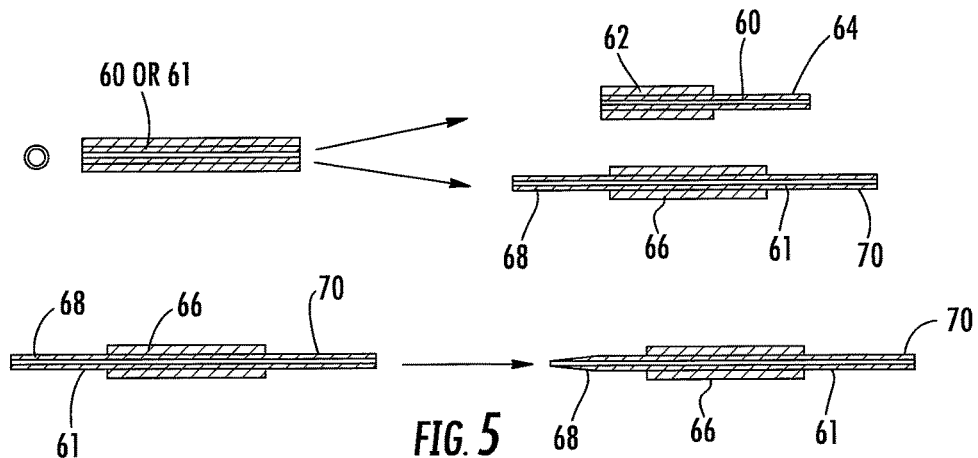
FIG. 5 depicts a non-limiting embodiment of how capillaries can be prepared for insertion by removal of a portion of the outer coating thereon.

(2) Referring to FIG. 5, provide a pair of fused silica capillary tubes 60 and 61 (e.g., 150 μm OD, 50 μm ID, 5 cm long, PolyMicro Technologies). Remove the outer coating material 62 from a portion of one end 64 of the first of the fused silica capillaries 60. Remove the outer coating material 66 from both ends 68 and 70 of the second fused silica capillary 61 (same type), and pull one end 68 of the second capillary 61 into a sharp tip (FIG. 5) so that one end 68 is sharp and narrowed and the other end 70 is blunt.

Figure 6:
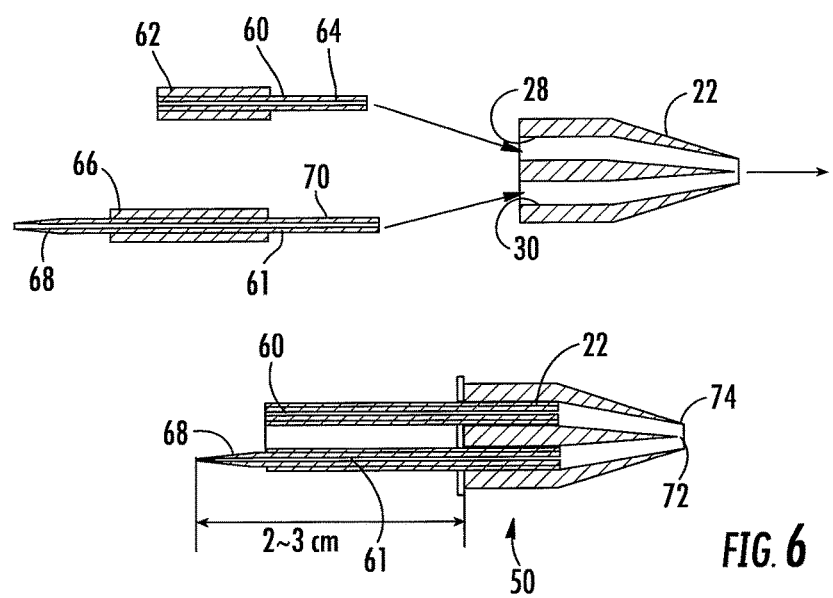
FIG. 6 depicts in a sectional view how the capillaries prepared in FIG. 5 are inserted into a pulled dual bore tube of FIG. 2 to form a Single-probe in accordance with one non-limiting embodiment of the present disclosure.

(3) Insert the exposed (decoated) blunt ends 64 and 70 of the two capillaries 60 and 61 into the bores 28 and 30 of the pulled glass tubing 22 obtained from step 1 (FIG. 2), seal gaps using UV-light active epoxy (e.g., Prime Dent Light Cure Resin Dental Bonding Adhesive), and irradiate the entire piece with UV light for 30 seconds to form the integrated Single-probe 50 (FIG. 6).

The Single-probe(s) 20 and 50 produced from Step 3 of either of Examples 1 or 2 may have slight deadspace 45 and 72 near the probe tip(s) 49 and 74, respectively. The solution containing analytes could be retained inside of the deadspace for a few more seconds (or fractions of seconds) before it is flushed by new solution which could slow down the detection speed. So, to solve this shortcoming, an alternative method is designed to fabricate a Single-probe 80 shown in Example 3.

Example 3

Figure 7:
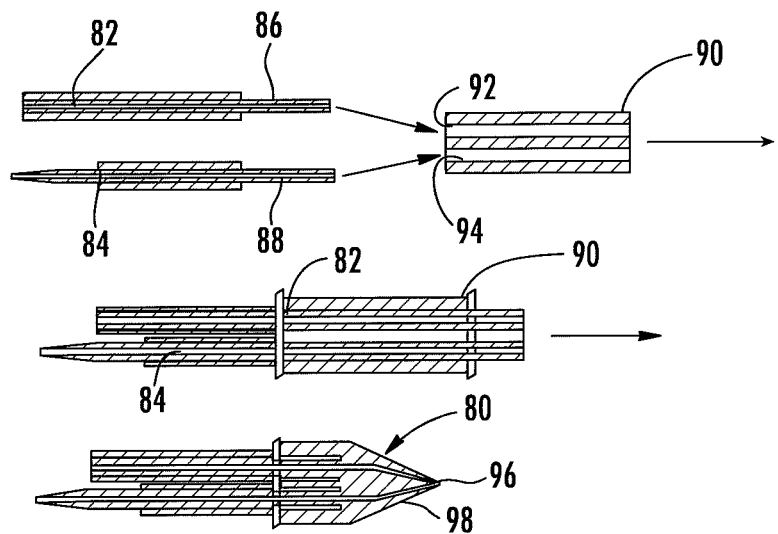
FIG. 7 depicts in a sectional view an alternate non-limiting embodiment of the present disclosure wherein a pair of capillaries as prepared in FIG. 3 can be inserted into a dual bore tube which is then pulled to form a narrow tip to form a Single-probe having a reduced deadspace in the junction tip.

Instead of pulling the fused silica capillaries and dual-bore glass tubing separately, as discussed above, insert decoated or uncoated blunt ends 86 and 88 of two fused silica capillaries 82 and 84, respectively, into a quartz dual-bore tube 90 having a first bore 92 and a second bore 94, glue both ends 86 and 88, and pull capillaries 82 and 84 and tube 90 all together using a laser puller (not shown) (e.g., such Sutter P-2000). The capillaries 82 and 84 and tube 90 melt simultaneously by leaser heating, and a similar Single-probe 80 with smaller deadspace 98 at the tip 96 is produced (FIG. 7).

Example 4

Figure 8:
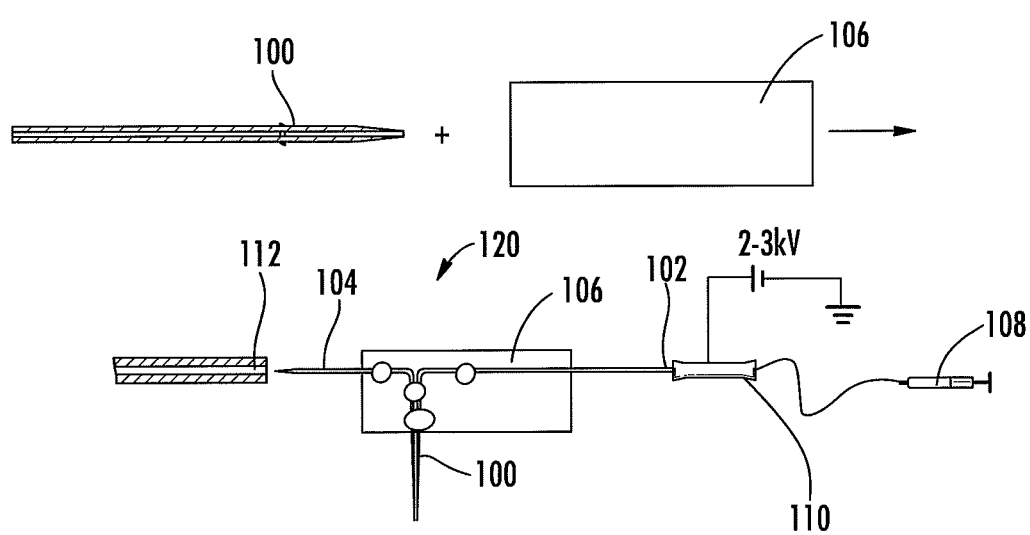
FIG. 8 depicts an experimental set up of a Single-probe MSI system of the present disclosure including a Single-probe on a support device which is attached via a micro-tight conductive union to a solvent supplying device.

The probe(s) from Examples 1-3, shown in FIGS. 4 and 8 as 100, or any other novel probe embodiment described herein can then be utilized with a MS apparatus to provide a Single-probe MSI system 120. For example, the probe 100 having a first end 102 and a second end 104 can be attached to a support 106 (e.g., a glass slide) for example using epoxy or glue. Connect the first end 102, which has a flat orifice, to a syringe 108 using a connector 110 such as a MicroTight Conductive Union (Upchurch Scientific); the voltage can be applied to the union. Attach the other end 104, which has a sharp emitter tip, to an inlet 112 of the mass spectrometer (not shown) (e.g., Thermo LTQ Orbitrap XL mass spectrometer). The system is ready for imaging measurement (FIG. 8). The Single-probe MSI system 120 can be used to measure a tissue 122 on an X-Y-Z movable system 124. In addition, the sharp tip can be inserted into a single cell, such that can directly detect the chemicals inside of cells. This feature of the Single-probe has not been obtained by using other current existing MSI techniques.

Example 5

Single Cell Mass Spectrometry

Figure 9:
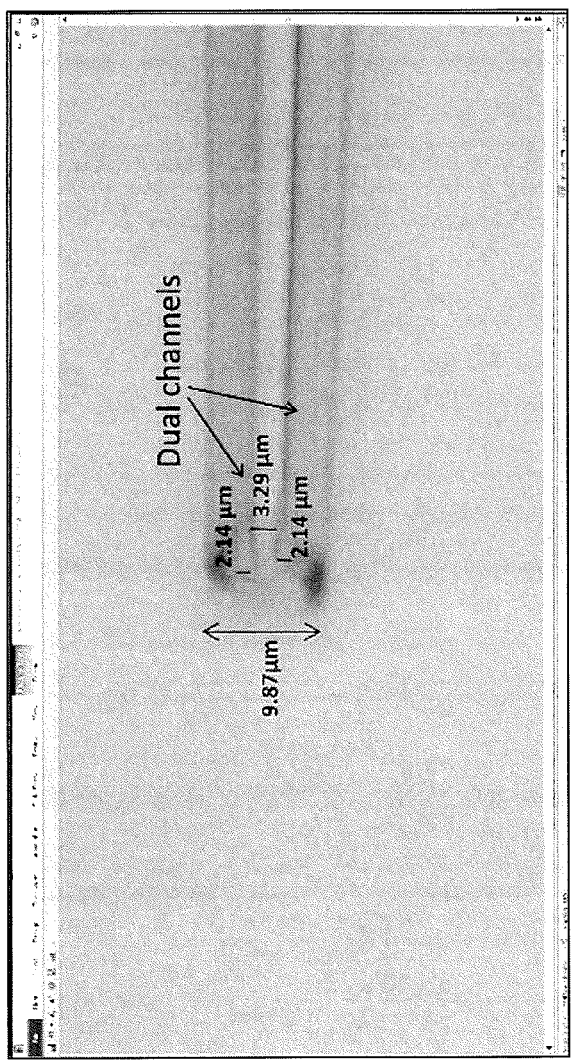
FIG. 9 is a photograph of a tip of the Single-probe in one non-limiting embodiment of the present disclosure. The bore dimensions of the probe, obtained using a digital microscope, are not limited to those shown in the photograph.
Figure 10:
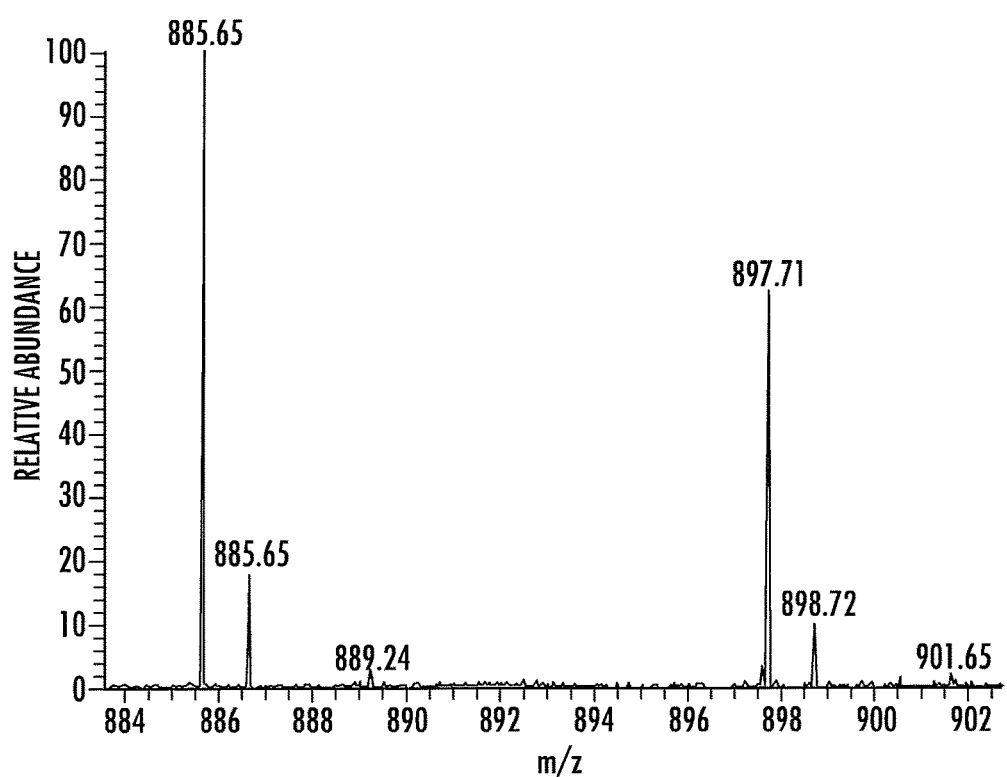
FIG. 10 depicts mass spectra obtained using a Single-probe inserted into a phosphate buffered saline (control) solution.
Figure 11:
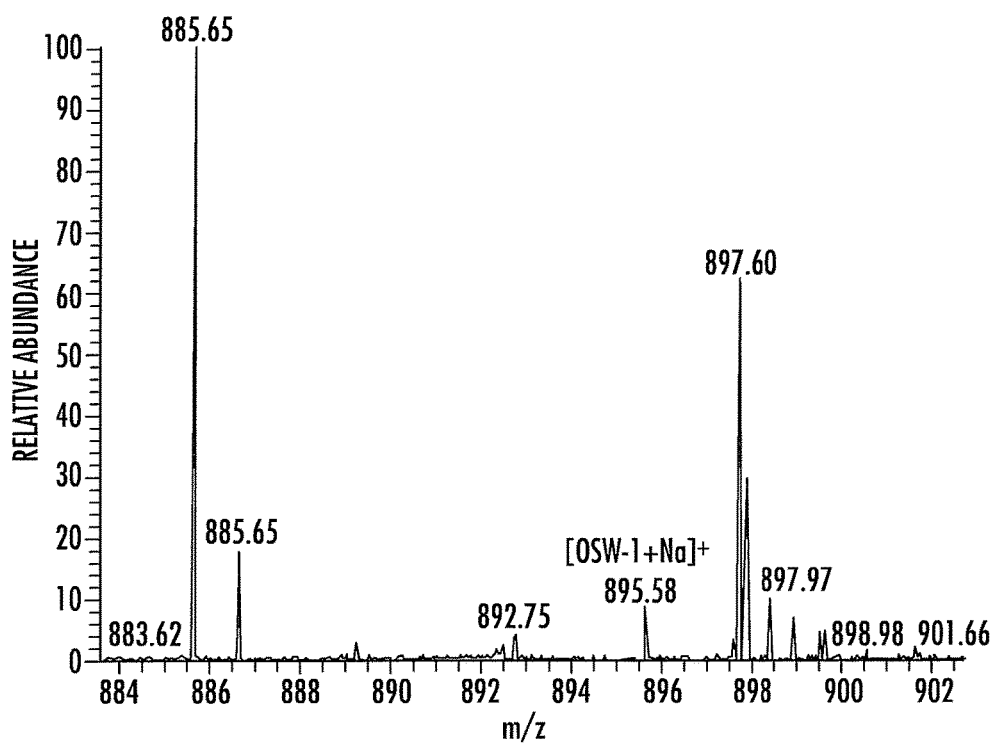
FIG. 11 depicts mass spectra obtained using a Single-probe inserted into a HeLa cell treated with OSW-1.

Similar to other high-resolution MSI newly described herein techniques, the Single-probe MSI can be used for single cell MS studies, in which the solvent droplet formed at the tip of the imaging probe can sample species inside of cells. Performing MS in living, single cells is potentially a major advancement in biological science, but only if it can be accomplished in situ in real-time, which other current techniques cannot achieve but is now achieved with the novel Single-probe described herein. Single-probe MS of single cells as enabled herein provides a novel way to understand the dynamic activities of the cell, particularly upon experimental stimuli. In fact, some cell lines critical for drug discovery studies, such as HeLa (cervical cancer) and NIH 3T3 (mouse embryonic kidney), are likely to be the best targets due to their relatively large size (>10 μm) and biological importance. In the presently disclosed inventive concepts, Single-probes having very sharp tips (e.g., having a tip diameter of 10 μm or less, e.g., see FIG. 9) can be fabricated. Such probe tip sizes are comparable in size to single cells. Experiments have been carried out on such cells using novel Single-probe devices such as disclosed herein. To demonstrate the ability of the Single-probe to measure and identify specific substances in a cell, HeLa cells were cultured and treated with OSW-1 (anti-cancer drug, 4 hours treatment). After being washed with PBS to remove OSW-1 present in the culture medium and absorbed on the cell surface, the cell-containing plate was placed under the Single-probe and a microscope (Supereyes T004 Electronic Digital Microscope). The Single-probe was inserted into cells by precisely lifting the z-translation stage (the minimum incremental motion of the stage is 0.1 μm), and the corresponding ion signals of OSW-1 species was monitored during the approach. Different spectra (FIG. 10) were observed while the imaging probe was still in the PBS (phosphate buffered saline) solution (before insertion into the cell), and after the probe was inserted into a single cell (FIG. 11). A significant change of the total ion intensities of OSW-1 species (m/z=895.58, sodium adduct ion) confirmed that OSW-1 was detected inside a single cell using the Single-probe MSI technique in situ and in real-time.

Example 6

The tips of the Single-probes of the presently disclosed inventive concepts can be formed to have extremely narrow diameters (e.g., as small as 0.03 μm). However, high electrical resistance, which is induced by extremely small inner diameters of channels inside of probe-tips and low electrical conductivity of solvent (i.e., methanol/water, acetonitrile), can hinder the sample ionization at the nanospray emitter end of the probe. For example, an ion signal can be difficult to observe when the tip size less than 8~9 μm, even though a smooth solvent flow can still be obtained from the primary capillary via a syringe, indicating that nanospray cannot be formed due to a significant voltage drop between the conductive union and nanospray emitter end of the probe. To overcome these obstacles, fabrication protocols of the imaging probe can be modified through three different approaches (FIGS. 12A-12F).

(a) Gold-coating nanospray emitters. The nanospray emitter capillaries inserted into the dual-bore quartz tube can be coated with gold or other conductive materials. Referring to FIGS. 12A and 12B, a pair of fused silica capillaries 130 and 132 having an outer coating material 136 are provided, as described herein in Examples 1-3. A tapered or sharp end 134 decoated of the outer coating material 136 of the capillary 132, used as the nanospray emitter, is coated with gold or other conductive materials. Additionally, a tube 138 having a first bore 140 and a second bore 142 is provided. The capillaries 130 and 132 are inserted into the first bore 140 and the second bore 142 of the tube 138, respectively, to form a probe 144 having a tip 146.

(b) Gold-coating pulled dual-bore quartz tubes. Referring to FIGS. 12C and 12D, a pair of fused silica capillaries 150 and 152 are provided, as described herein in Examples 1-3. Capillary 152 is provided with a tapered or sharp end 154 decoated of an outer coating material 156 of the capillary 152, used as the nanospray emitter. Additionally, a tube 158 having a first bore 160 and a second bore 162 is provided. The dual-bore quartz tube 158 which have been pulled (sharpened to a point) can be coated (e.g., by UHV Sputtering, Inc.) with gold or another conductive coating (e.g., coating having a thickness <1 μm). The capillaries 150 and 152 are inserted into the first bore 160 and the second bore 162 of the tube 158, respectively, to form a probe 164 having a tip 166. (FIGS. 12C and 12D).

Figure 13:
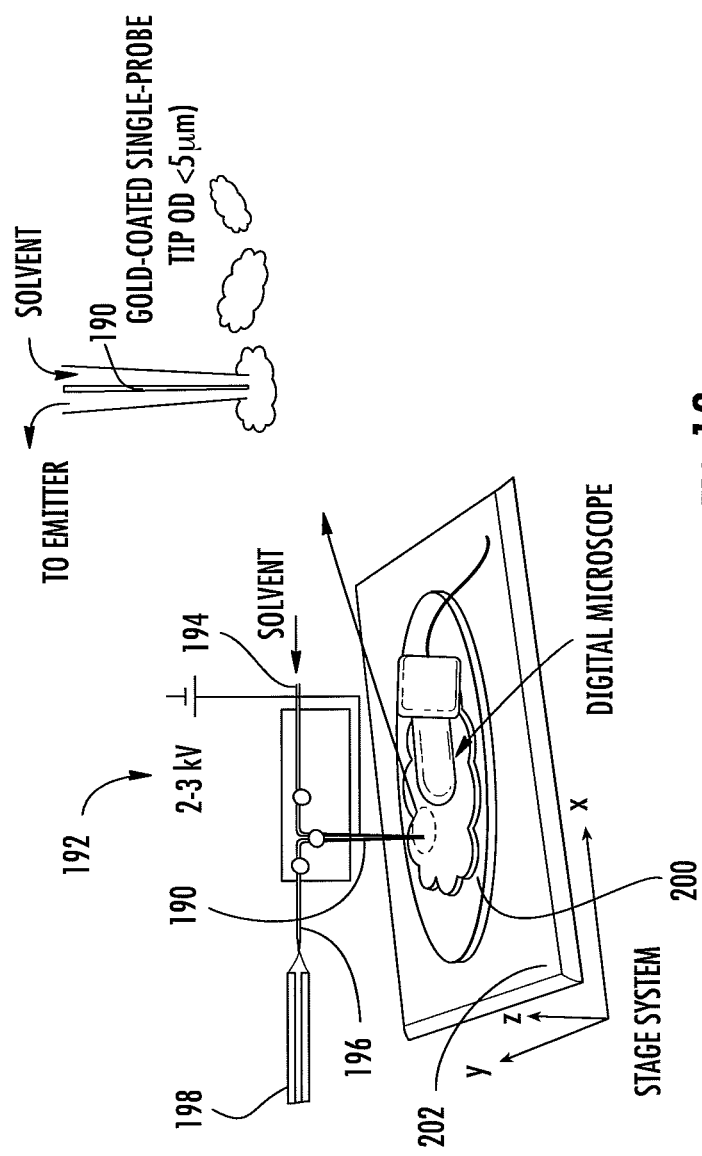
FIG. 13 depicts a non-limiting embodiment of a system of the present disclosure which uses a probe such as constructed in FIG. 12. An ionization potential is directly applied to the conductive coating on the low deadspace Single-probe.

(c) Gold-coating small dead-space Single-probes. Imaging probes fabricated through approaches a and b above may have a relatively large dead-space ("dead-volume") at the tip junction of the two capillaries. The effects of a dead-space become more pronounced in the case of analyzing a single cell. For example, the volume of a single cell (~10 μm diameter) is estimated to be only a few pico-liters. Referring to FIGS. 12E and 12F, to obtain a Single-probe 170 with a small volume dead space, fused silica capillaries 172 and 174 (with smaller ID) can be inserted through quartz dual-bore tubing 176, both ends glued, and pulled together using the laser puller. The capillaries and tubing will melt by laser heating and be simultaneously pulled forming a Single-probe 170 having low dead-space (low dead-volume) 178, which will be coated with gold or other conductive material 180 in a further step. Such coated probes produced from the methods described herein are coupled with a MSI device, and the ionization voltage can be directly applied to the gold coating (e.g., a low dead-space probe is represented in FIG. 13 as an example). Referring to FIG. 13, such a gold coated probe(s) 190 is shown utilized with a MS apparatus to provide a Single-probe MSI system 192. For example, the probe 190 having a first end 194 and a second end 196 can be attached to a support 198 (e.g., a glass slide) for example using epoxy or glue. The first end 194, which has a flat orifice, is used to provide a solvent. Voltage can be applied to the gold coating of the probe 190. The second end 196, which has a sharp emitter tip, is connected to an inlet 198 of the mass spectrometer (not shown) (e.g., Thermo LTQ Orbitrap XL mass spectrometer). The Single-probe MSI system 192 can be used to measure a tissue 200 on an X-Y-Z movable system 202.

Example 7

Using the present methods and probes, the actual abundance of a therapeutic molecule in a single cell can be determined. For example, the absolute abundance of deguelin inside single cells can be determined. For example, to measure OSW-1, a deuterated OSW-1 (OSW-1d) analog is used as an internal standard compound. The OSW-1d with known concentration is added into the solvent used to sample the analytes inside single cells. The OSW-1 present inside a cell is sampled and ionized, and its ion intensities are reported relative to the OSW-1d internal standard (e.g., normalization). The absolute abundance of OSW-1 is derived by integrating a set of results such as the relative ion intensities of OSW-1 and its deuterated form, the concentration of OSW-1d, the flow rate of international standard solution, and the MS accumulation time.

Example 8

As indicated above, when coupled with mass spectrometry (MS), the Single-probe of the presently disclosed inventive concepts can be used for the analysis of single eukaryotic cells and for the measurement of spatial distribution of chemicals on biological tissues. Additionally, the device can be used for the detection of proteins with posttranslational modifications (PTMs). Some of the most common post-translational modifications (PTMs) of proteins involve sulfation, phosphorelation, and/or carboxylation. Recently, the detection of the sulfated peptides has become an important topic in mass spectrometry (MS). Previous studies have been conducted using nano-electrospray ionization (nano-ESI) and desorption electrospray ionization (DESI) both with low pH sample solutions. However, the detection of sulfated peptides in the positive ion mode (common for proteomics studies) is hampered due to their rapid hydrolysis in solution.

Figure 14:
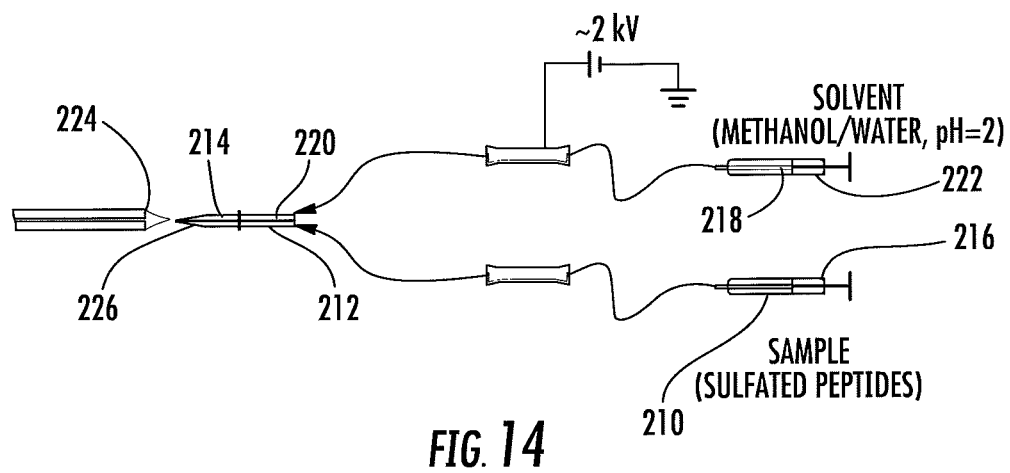
FIG. 14 depicts a system for detection of posttranslational modifications (PTMs).

Using the Single-probe MS technique of the present disclosure, as described herein, sulfated peptides and proteins can be detected. In one experiment for example, referring to FIG. 14, sulfated proteins are prepared in MeOH:$H_2O$ solution 210, and infused into one capillary 212 of the Single-probe 214 using a syringe 216. Acidic MeOH:$H_2O$ solution with pH=2 218 (using HCl) is infused into the other capillary 220 with a syringe 222 to enhance the ionization efficiency of proteins. The Single-probe 214 is placed towards the MS inlet 224 as explained elsewhere herein and the ionization potential (~2 kV) is applied. Two solutions are rapidly mixed at the probe tip 226, and the reaction time allowed for hydrolysis is significantly shortened; however, proteins are protonated due to the extremely fast reaction rate of protonation processes. Experimental results indicate that intact sulfated or phosphorylated protein ions were dominant, whereas the corresponding desulfation species was significantly reduced or completely eliminated.

Example 9

Use of the Single-probe with a Micro-funnel for extracellular compounds analysis.

Above, a Single-probe device MS for analysis of compounds inside single cells is described. In fact, single cell level measurement of both intracellular and extracellular compounds has been a long-sought goal of biological and pharmaceutical studies. Especially, current single-cell MS developed techniques are unable to analyze living cells interacting with their surrounding normal environment and other cells. The MS analysis of small-molecular weight compounds excreted by mammalian cells, the lipid and metabolite components of the secretome, has not been extensively studied on the single cell level, due to the lack of analytical detection methods. The uncharted area of single cell non-protein secretome analysis holds a tremendous amount of promise.

Figure 15:
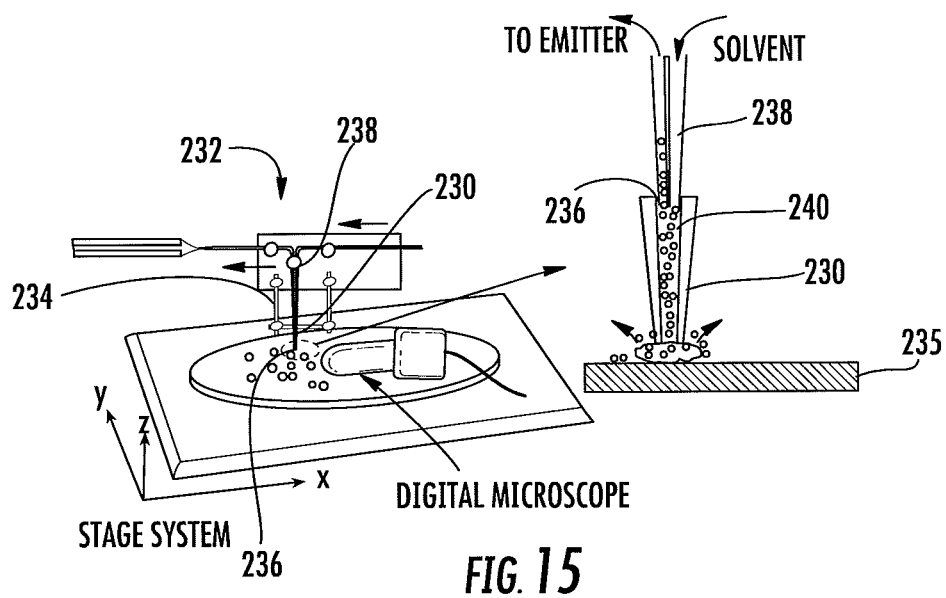
FIG. 15 depicts a probe and system which uses a "microfunnel" in accordance with an embodiment disclosed herein.

In an alternative embodiment of the presently disclosed inventive concepts, a 'micro-funnel' adapter 230 for a Single-probe system 232 has been developed (FIG. 15). The Single-probe system 232 is similar to the Single-probe system(s) 192 (FIG. 13) except as described herein. The micro-funnel component 230 can be supported on a scaffold 234 that is built from thin fused silica capillary (e.g., 90 µm outer diameter). The scaffold 234 is thin enough to allow the micro-funnel component 230 to access a cell surface 235 while rigid enough to maintain stable structure during the sampling and MS measurement processes. The tip 236 of the Single-probe 238 is inserted into an upper orifice 240 of the micro-funnel component 230 to sample the chemical species inside the funnel 230. The micro-funnel 230 of the probe 238 is placed at the cell surface 235 to collect excreted molecules over the time (e.g. ~20 minutes) before MS analysis through the Single-probe 238. The Single-probe 238 is activated inside of the micro-funnel 230, to draw the solution there to the nano-ESI emitter via capillary action. The solvent used in the Single-probe 238 may be for example, either an aqueous buffer or an organic solvent, for example, that provides for better ionization efficiency. In one non-limiting embodiment the micro-funnel 230 is fabricated from a fused silica capillary pulled by laser puller. After pulling, it into a small piece (e.g., length: ~5 mm; upper opening OD: ~100 um, ID: 40 um; lower opening OD: 8-10 um, ID: ~5 um). The Single-probe tip 236 is inserted into the upper opening 240 of the micro-funnel 230. They can be held together through a scaffold 234 (e.g., made from fused silica capillaries). The internal volume of the micro-funnel 230 in this embodiment is in a range of from about 25 nL to about 200 nL, e.g., about 100 nL.

Example 10

In another embodiment, the present disclosure provides a new method to assess cellular targets of drug-candidate compounds using a newly devised nanoscale mass spectroscopic and protein separation technologies. With current experimental methods, it can be very difficult to identify the cellular target of a biologically-active small molecule. Inside of the cell, there are thousands of different proteins capable of interacting with a drug-candidate molecule, but only a tiny subset of all the cellular proteins are targeted by the biologically-active small molecule. This specific interaction between the small molecule and its protein target(s) triggers the cellular response leading to the observed biological activity of the small molecule. Without understanding how the drug-candidate compound triggers it biological-activity through binding its cellular target, therapeutic development for that compound cannot proceed.

Currently, the typical experimental approach to identifying the cellular target of a small molecule consists of affixing the compound to a solid resin, and then using this affinity resin to enrich for proteins that bind to the resin affinity chromatography). In order to affix the compound to the resin, this approach requires the ability to modify a position on the compound's structure without destroying its bioactivity. Additionally, this approach requires a relatively large amount of drug-candidate compound (e.g., >10 mg), and often this expensive, slow and labor-intensive experimental approach is not applicable nor successful for many compounds.

Figure 16:
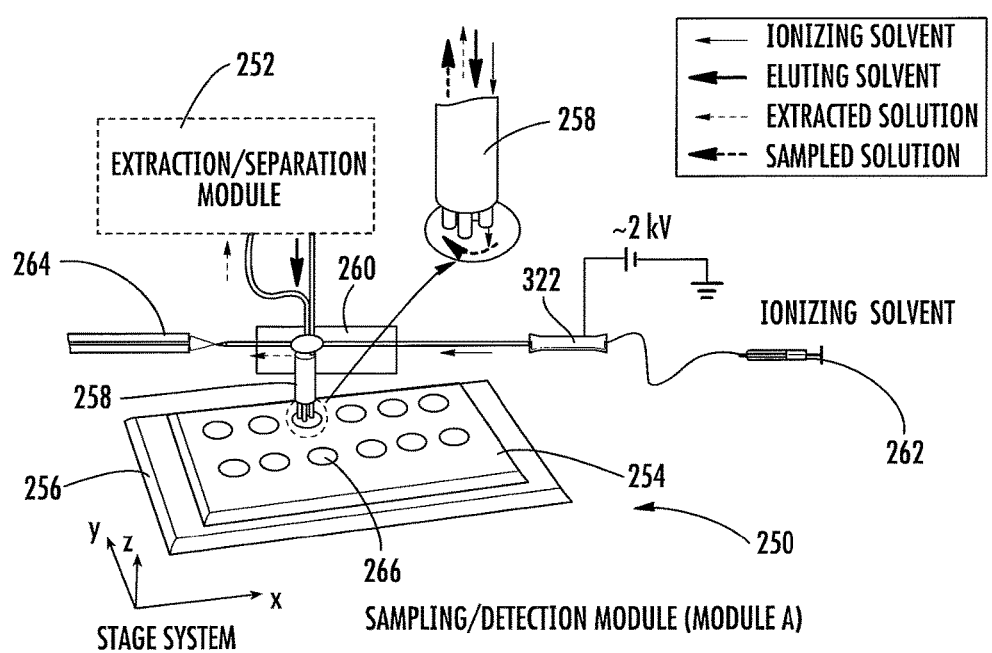
FIG. 16 depicts a system of the present disclosure using a sampling/detection module and an extraction/separation module utilizing a 4-bore probe.
Figure 17:
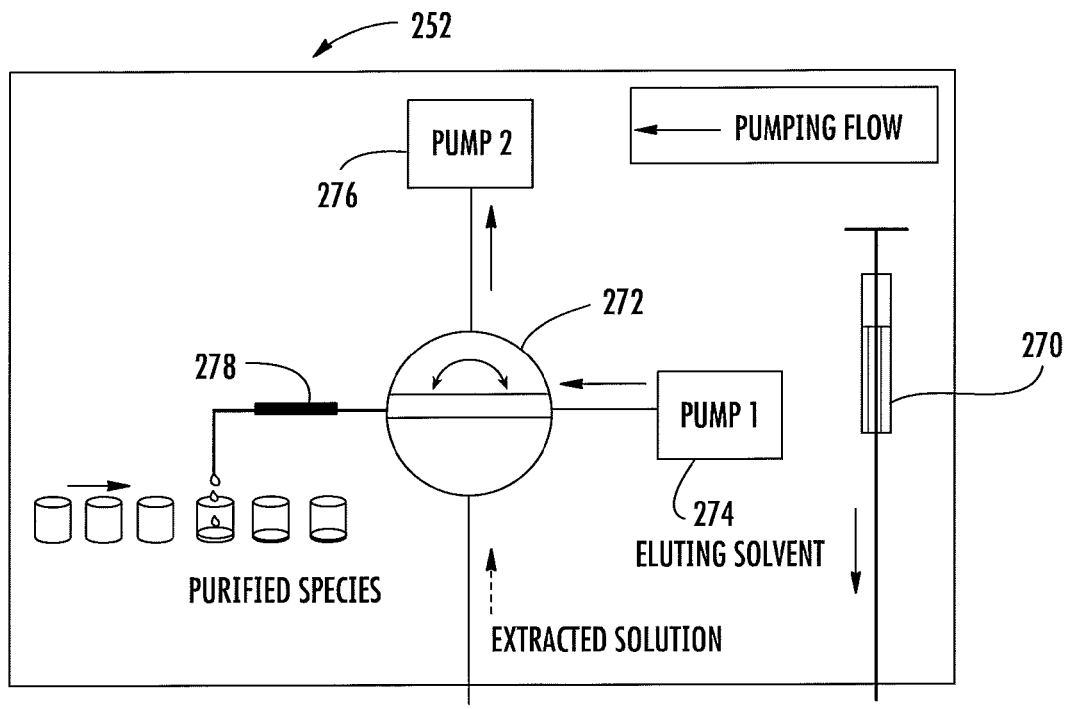
FIG. 17 depicts a micro-fabrication based capillary extraction/separation module used in FIG. 16.

In this embodiment of the presently described inventive concepts, a system for the rapid identification of a compound's cellular target without affinity-chromatography nor any chemical modification of the compound's structure is described. This system rapidly identifies the cellular target (s) using a miniscule amount of drug-candidate compound. The system is based on applying novel microscale bioseparation methods in conjunction with the newly proposed nanoscale mass spectrometric sampling and separation instrumentation described herein to identify the cellular targets of drug-candidate compounds. The system described herein includes two novel instrumentation/technology modules. Module A described herein is a mass spectrometry based sampling and detection device 250 (FIG. 16), and Module B is a micro-fabrication based capillary extraction and separation apparatus 252 (FIG. 17). In this system for example, a drug-candidate compound is mixed with a cellular lysate containing multiple (e.g., up to thousands) different proteins. This compound/lysate mixture is subjected to a microscale bioanalytical purification step to produce separate fractions that contain a limited number of proteins in each (e.g., about 10 proteins). The fractions are spotted as microdroplets on a surface, and then Module A and Module B are employed to (1) locate the drug-candidate compound in the multitude of microdroplets and (2) to identify the proteins that have co-purified with the compound, revealing putative cellular targets.

Referring to FIGS. 16-22, the mass spectrometry based sampling and detection device (Module A) 250 includes a multi-well sample feeder 254 mounted on a translational stage system 256, a multi-bore sampling and ionizing probe 258, a support 260, an ionizing solvent syringe 262 connected to an end of the probe 258 and a mass spectrometer inlet 264. The mass spectrometry based sampling and detection device (Module A) 250 is operationally connected to the micro-fabrication based capillary extraction and separation apparatus (Module B) 252. The micro-fabrication based capillary extraction and separation apparatus (Module B) 252 includes a syringe 270, an extraction pump device 272 having a first pump 274 and a second pump 276 and a separation column 278.

Major Components of Module A (a) Multi-well (vial) sample feeder. The drug-target containing solution is saved in the wells 266 on the plate or vials on the rack that are mounted on the translational stage system 256. The sample is fed by controlling 3 translational stages (x, y, and z directions) via a computer program.

Figure 18:
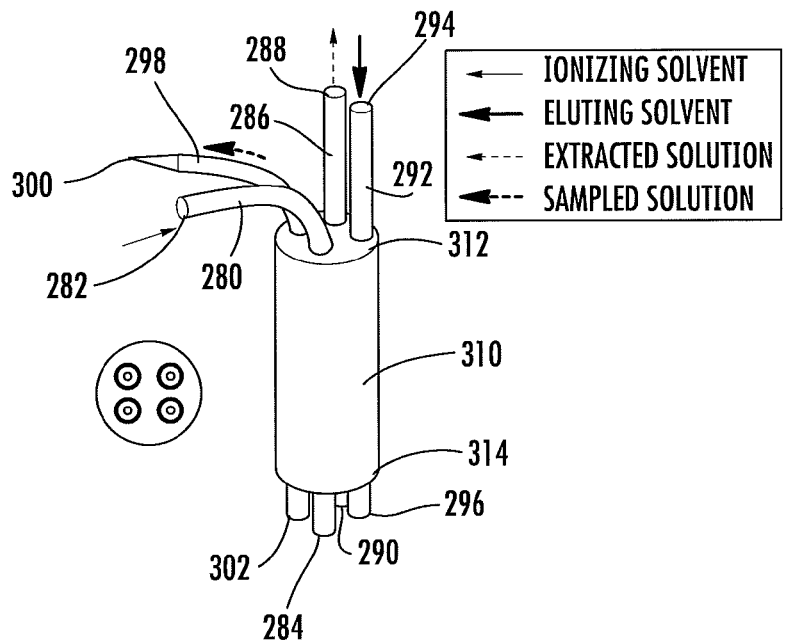
FIG. 18 depicts a non-limiting embodiment of a 4-bore sampling-ionizing probe used in the sampling/detection module of FIG. 16.
Figure 19:
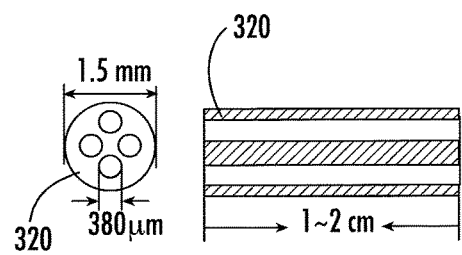
FIG. 19 depicts a 4-bore tube used in the fabrication of the 4-bore probe of FIG. 18.
Figure 20:
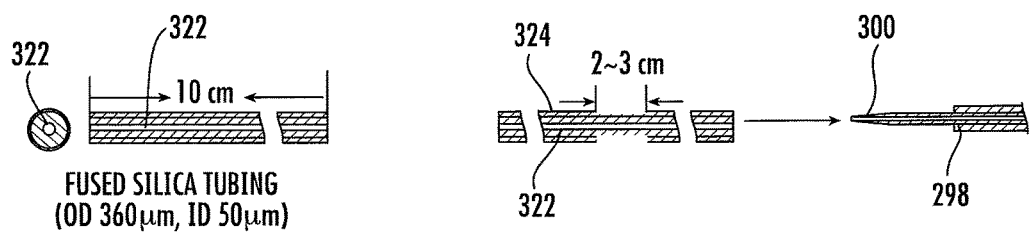
FIG. 20 depicts capillaries with portions of the coating removed therefrom for fabrication into emitter capillaries.
Figure 21:
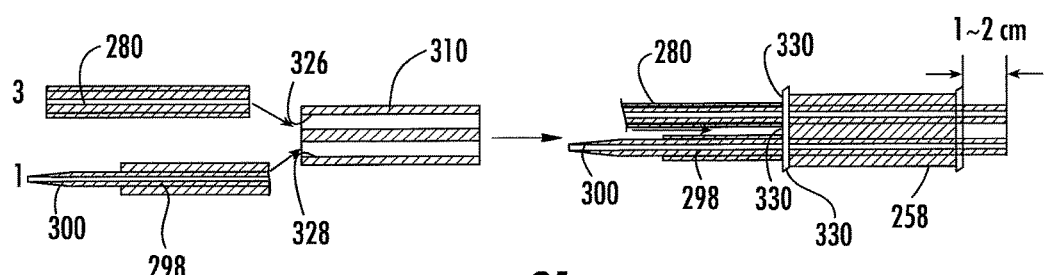
FIG. 21 depicts capillaries inserted into the 4-bore tube to form the 4-bore probe.

(b) Multi-bore sampling and ionizing probe. This novel probe 258 is fabricated by inserting 3 fused silica capillaries 280 having a first end 282 and a second end 284, 286 having a first end 288 and a second end 290 and 292 having a first end 294 and a second end 296 and 1 nano-ESI emitter (narrow tip) fused silica capillary 298 having a first end 300 and a second end 302 into a multi-bore glass tube 310 having a first end 312 and a second end 314 (FIG. 18).

Working Mechanism of Module A

In one the experiment, the ionizing solvent (e.g., methanol/water solution) is supplied by one capillary 280, and mixed with sample solution (cell lysate) inside of wells 266 or vials. Due to the self-aspiration of liquid inside of capillary 280, the analyte of interest (e.g., drug-target complex) can be sucked to the nano-ESI emitter 286. An ionization voltage (~2 kV) is applied between the emitter 286 and the inlet of a mass spectrometer 264, and therefore the analytes are ionized here and analyzed by the mass spectrometer. The action of Module B 252 and the stage system 256 depend on the mass spectrometry results. A positive result, in which the species of interest are detected from the sample, will trigger Module B 252 and initiate the infusion of eluting solvent, the suction of analyte containing solution, and separation/collection of analyte. Once these processes are finished, the stage system 256 will move the next sample for analysis. In contrast, a negative result will only result in the motion of the stage system 256.

Fabrication of Module A (a) Multi-well (vial) sample feeder. The core component of this device is the stage system 256, including 3 independently controlled translational stages (for x, y, and z motion) and the controlling software. A similar system for mass spectrometry imaging measurement was established, in which the sample is mounted on a holder of the stage system 256. The sample position is controlled by the motion of these 3 translational stages under the command of a LabView program. The hardware of the current system can be directly used for the innovation, whereas a modification of control software can be made for the synchronized action of Modules A and B.

Figure 22:
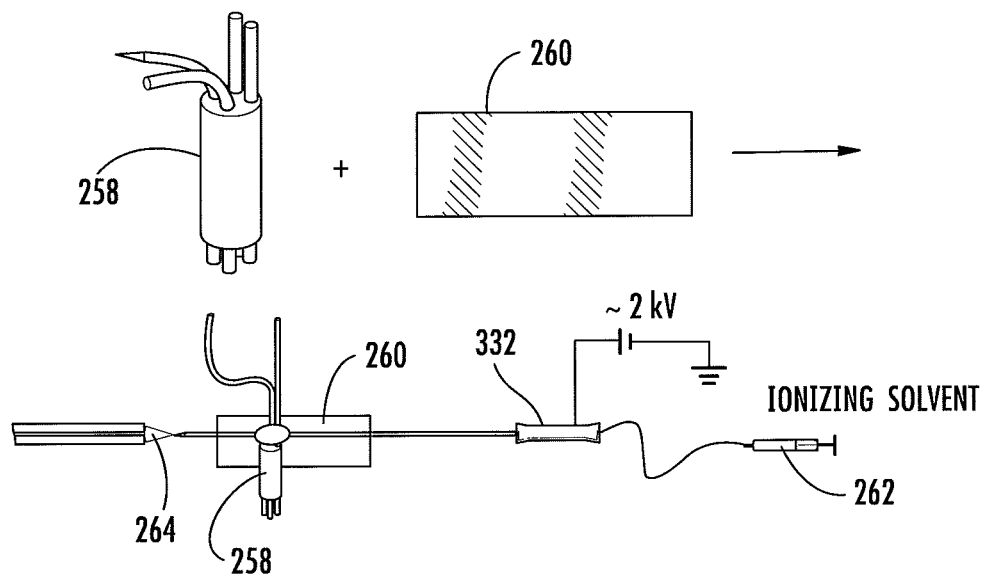
FIG. 22 depicts a non-limiting embodiment of the 4-bore probe implemented into an analysis system including an ionizing solvent.

(b) Multi-bore sampling and ionizing probe. The probe 258 is an integrated part for multiple functions. It enables the sampling of small amounts (e.g., <10 nL) of solution, ionization of the solution for mass spectrometry analysis, infusion of an eluting solvent into the solution, and extraction of the analyte containing solution for separation. Due to its small physical size (e.g., OD=1.5 mm) and low sampling volume, the probe 258 can be used to detect and extract species of interest from small amounts of samples. The multi-bore probe 258 can be directly exchanged with the dual-bore Single-probe described elsewhere herein, which is for the mass spectrometry imaging studies, to detect sample solution using mass spectrometer. One non-limiting embodiment of how the multi-bore Single-probe 258 can be fabricated is described as follows:

(1) Cut the multi-bore glass tube 320 (1.5 mm OD, 380 µm ID, Friedrich & Dimmock, Inc.) intol ~2 cm long pieces (FIG. 19), (2) Cut the fused silica capillary 322 (360 µm OD, 50 µm ID, PolyMicro Technologies) into 4 pieces (~10 cm long). Remove the coating material 324 (~3 cm long) in the middle of 1 tubing piece, and pull it into 2 pieces with a sharp tip one end 300 by using a laser puller (e.g., Sutter P-2000) to form the nano-ESI emitter (narrow tip) fused silica capillary 298 (FIG. 20), (3) Insert the blunt (flat) ends 284, 290, 296 and 302 of the 4 fused silica capillaries 280, 286, 292 and 298 (represented by 280 in FIG. 21) into the bores 326 and 328 of the 4-bore glass tube 310, and leave these ends 1-2 mm beyond one end 314 of the 4-bore tube 310. The narrow tip 300 of the nano-ESI emitter 298 and opposite blunt tips 282, 288 and 294 of the other three capillaries 280, 286 and 292 extend beyond the opposite end 312 of the 4-bore tube 310. Seal gaps 330 (e.g., using UV-light active epoxy-Prime Dent Light Cure Resin Dental Bonding Adhesive), and irradiate the whole piece with UV light for 30 seconds. The multi-bore sampling and ionizing probe 258 has been produced (FIG. 21), and (4) Integrate small parts into a unit probe device (FIG. 22). First, attach the multi-bore sampling and ionizing probe 258 to the support 260, e.g., a glass slide, using epoxy or glue. Second, make the connection between the probe 258 and the sampling/ionization circulation. Connect the blunt end of one fused silica capillary to the syringe 262 using the MicroTight Conductive Union 332 (Upchurch Scientific); the voltage can be applied to the union. Attach the other end 300, which has the sharp narrow emitter end, to the inlet 264 of the mass spectrometer. Third, make the connection between the probe 258 and the extraction/separation circulation 252. Connect the blunt end 294 of one fused silica capillary 292 to the syringe pump of Module B, which provides the eluting solvent. Connect the end 288 of the last fused silica capillary 286 to the extraction pumping device 272, which is connected with the separation column 278.

Certain embodiments of the probes of the present disclosure can be constructed with tubes having two or more bores, including dual-bore tubes, three-bore tubes, four-bore tubes, and other multi-bore tubes having for example 5, 6, 7, 8, 9, 10, or more separates bores. The ID of the bores of the tubes may be in a range of, but are not limited to, 1 µm to 500 µm, for example 5 µm to 400 µm, 10 µm to 300 µm, 20 µm to 200 µm, 5 µm to 200 µm, or any subrange of integers inclusive within the range 1 µm to 500 µm, such as 25 µm to 125 µm.

The capillaries used to make the probes (which are inserted into the tube bores) can have an ID in a range of, but not limited to, 1 µm to 150 µm, for example 5 µm to 150 µm, 10 µm to 100 µm, 20 µm to 750 µm, 25 µm to 50 µm, or any subrange of integers inclusive within the range 1 µm to 150 µm, such as 20 µm to 60 µm. The capillaries can have an OD in a range of, but not limited to, 5 µm to 450 µm, for example 10 µm to 350 µm, 20 µm to 300 µm, 40 µm to 250 µm, 50 µm to 200 µm, or any subrange of integers inclusive within the range 5 µm to 450 µm, such as 75 µm to 150 µm.

In certain embodiments, the tip of the probe of the present disclosure may have an OD in a range of, but not limited to 0.03 µm to 50 µm, for example 0.1 µm to 50 µm, 0.5 µm to 30 µm, 1 µm to 25 µm, 1.5 µm to 20 µm, 2 µm to 15 µm, or any subrange of integers or fractions inclusive within the range 0.03 µm to 50 µm, including, but not limited to 1 µm, 1.5 µm, 2 µm, 2.5 µm, 3 µm, 3.5 µm, 4 µm, 4.5 µn, 5 µm, 5.5 µm, 6 µm, 6.5 µm, 7 µm, 7.5 µm, 8 µm, 8.5 µm, 9 µm, 9.5 µm, 10 µm, 10.5 µm, 11 µm, 11.5 µm, 12 µm, 12.5 µm, 13 µm, 13.5 µm, 14 µm, and 14.5 µm.

Example 11

Figure 23:
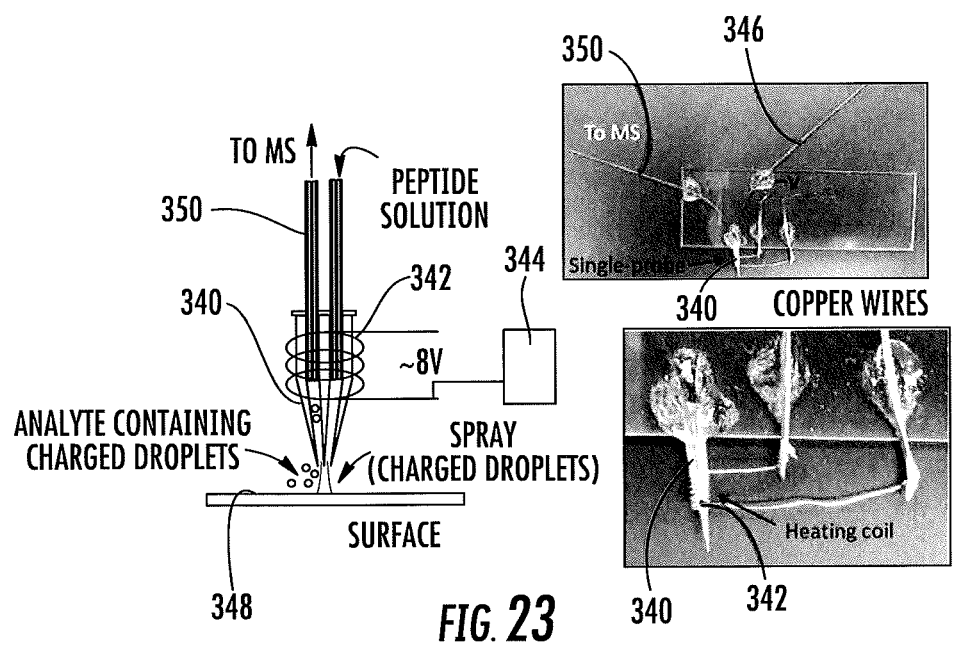
FIG. 23 depicts an alternate embodiment wherein a portion of the probe is heated.

In other embodiments of the present disclosure, the probes comprise means for heating at least a portion of the probe. One non-limiting example of such a heated probe 340 is represented in FIG. 23, wherein a miniaturized heating coil 342 is wrapped around the Single-probe 340, and a power supplier 344 is used to apply a voltage (e.g., ~7-8 V) to the coil 342 (e.g., Cr—Ni filament, gauge 34). The solvent (e.g., methanol/water mixture), which is carried by a solvent providing capillary 346, is heated up and sprayed as charged droplets onto the surface of the sample 348. Analytes on the surface of the sample 348 are desorbed, ionized, and sucked into the other capillary 350, which is connected to an MS inlet (not shown), for MS analysis as described elsewhere herein.

The desorption and ionization mechanisms of the heated Single-probe MSI have some similarities to DESI (desorption electrospray ionization), a popular method for MS analysis of surfaces and tissue imaging. Advantages of the heated Single-probe MSI technique include less clogging (no surface contact and larger orifice), less carry-over from the previous measurement, and shorter time delay (no liquid but only gas flow in the nano-ESI emitter channel). Although heated Single-probe MSI has some similarities to DESI, heated Single-probe MSI provides a higher analyte resolution due to its small tip size (i.e., smaller sampling area).

Example 12

In another embodiment, the Single-probe ion source is capable of producing strong ion signals of biochemical such as sulfoproteins in an analytical system 360 using a Single-probe 362 with LC-MS (FIG. 24). For practical LC-MS analysis, the outlet 364 of the LC 366 is connected to one of the capillaries 368 of the single-probe 362 of the presently disclosed inventive concepts, and a source 370 of an ionization solvent is connected to the solvent-providing capillary 372 of the single-probe 362. The post-column 374 of Single-probe 362 acts as the ionization source for the mass spectrometer (FIG. 24). The Single-probe 362 acts as the ionization source for the mass spectrometer, following separation of a mixture of proteins by liquid chromatography. During the process, the mixed proteins or peptides (or other analytes) are injected into the LC 366 and fractionated by the column 374. The separated proteins or peptides, including the sulfated species pass though the capillary 368, are ionized by the single-probe 362 and are detected by the MS. This post-LC column Single-probe design 360 can be used for regular LC-MS studies. For example, experimental results show that it is a very sensitive technique for analysis of samples containing sulfated proteins or peptides.

Example 13

An alternate embodiment of a single probe of the present disclosure is designated herein as a "T-probe" designated by reference numeral 390, which can be used, for example, for single cell analysis. The T-probe embodiment 390, as represented in one embodiment in FIG. 25(a), includes a polymeric substrate 392. The polymeric substrate 392 is constructed of a pair of flat polymeric sheets bonded together. The polymeric substrate 392 has a first bore 394 and a second bore 396 which intersect at a junction 398. The first bore 394 has a first tapered capillary tip 400 extending from a first end 402 thereof and a second tapered capillary tip 404 extending from a second end 406 thereof. The junction 398 is at a position between the first tapered capillary tip 400 and the second tapered capillary tip 404 such that a solvent introduced into the second bore 396 via a solvent capillary 397 flows through the junction 398 into the first bore 392.

The first tapered capillary tip (sampling tip) 400 samples the compounds inside a single cell and the second tapered capillary tip 404 is a nano-ESI emitter to ionize the sampled species for delivery to the MS. In the embodiment shown in FIG. 25(a), these three components are sandwiched between two polycarbonate slides and have ends which are connected at the T-junction 398. During sampling, the first tapered capillary tip 400 is inserted into a cell, and the cellular constituents are extracted and drawn to the T-junction 398, where they are mixed with the ionization solvent, then are ionized and emitted from the second tapered capillary tip 404/nano-ESI emitter to the MS where the samples are analyzed.

Figure 25B:
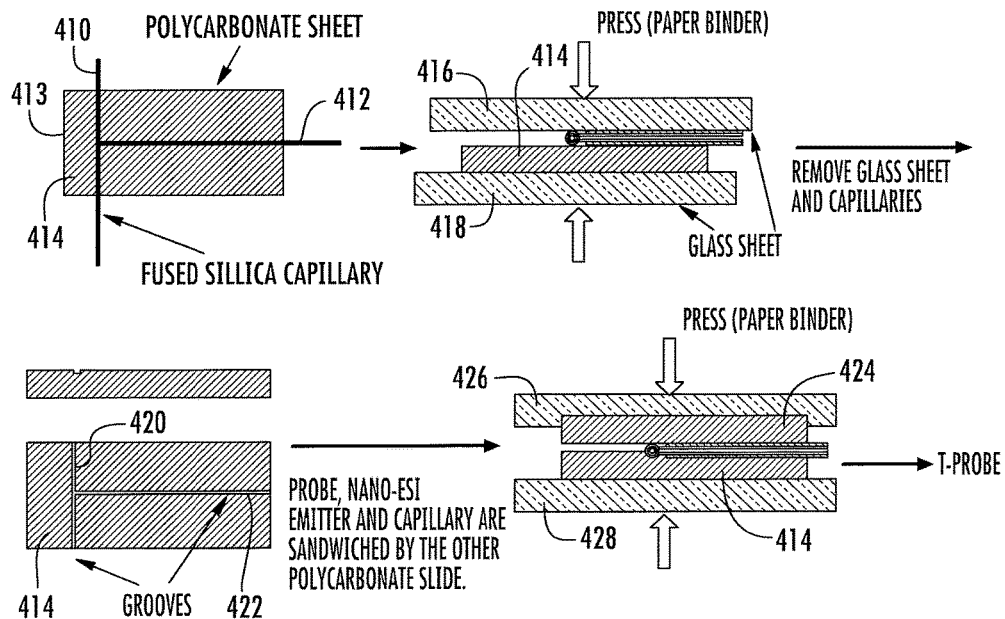
FIG. 25(b) depicts a fabrication protocol for the T-probe of FIG. 25(a).

One non-limiting version of how the T-probe 390 can be fabricated, comprising multiple steps, is explained below and shown in FIG. 25(b). First, two perpendicular silica capillaries 410 and 412 that have been fused into a T-shape 413 are placed on a polycarbonate sheet 414 (e.g., a microscope slide) then sandwiched between two glass microscope slides 416 and 418. The sandwiched stack is baked in an oven, e.g., at 70° C. for 4 hours, such that the fused capillaries 410 and 412 imprint two grooves 420 and 422 (T-shaped) on the polycarbonate sheet 414. Second, the sampling tip (first tapered capillary tip 400), the nano-ESI emitter (second tapered capillary tip 404), and the solvent capillary 397 are placed into the grooves 420 and 422 on the polycarbonate sheet 414 prepared from the previous step, and another polycarbonate sheet 424 is placed thereon to form a sandwich structure. The polycarbonate sandwich is clamped between two glass slides 426 and 428 and baked in an oven at 70° C. for 4 hours to bind the two polycarbonate sheets 414 and 424 together to form a T-probe 390 therein.

Figure 25C:
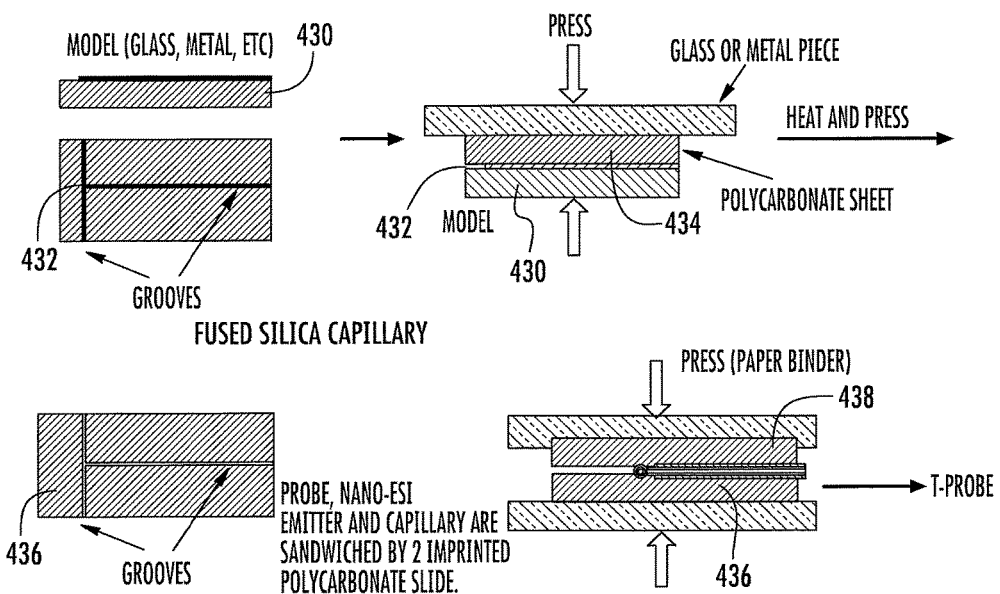
FIG. 25(c) depicts an alternate protocol for the fabrication of the T-probe.

An alternative protocol for making the T-probe 390 is illustrated in FIG. 25(c). Instead of using capillaries to imprint grooves on the polycarbonate slides, the grooves can be imprinted using a model 430 or template made of metal, glass, ceramic, or other suitable material machined or moulded to have a convex T-shape 432 on the model's surface. In a first step, the model 430 is used to imprint T-channels 432 onto a polycarbonate sheet 434 (optionally under heat) forming a channelized polycarbonate sheet 436. A sampling tip (such as first tapered capillary tip 400), a nano-ESI emitter (such as second tapered capillary tip 404), and a solvent capillary (such as solvent capillary 397) are positioned upon the channelized polycarbonate sheet 436 which is sandwiched with a second polycarbonate sheet 438 as shown in FIG. 25(*a*). This sandwich structure will be clamped and bound to produce a T-probe 390. Using an imprinting model can simplify the assembling procedures and may enable more rapid fabrication of the T-probes.

The T-probe versions of the probing device of the present disclosure has certain advantages over the dual-bore Single-probe for single cell analysis. One of the advantages is smaller tip size for sampling. Because there is only one channel inside of the sampling tip, rather than two or more, the sampling tip of the T-probe can be made even smaller and more narrow than the tip of the dual-bore single-probe. A smaller tip size allows for use on smaller cells. In addition, in certain embodiments, a small tip (e.g., 1 μm) may fuse with a living cell, which may make it possible to monitor the chemical change inside of the single cell in terms of time or environment change (e.g., temperature, drug concentration, cell living medium). Another advantage of the T-probe is reduced perturbation of the intracellular environment. When the Single-probe is used to sample the cellular contents, the ionization solvent (inorganic or organic) must be introduced into the cell. This introduction of solvent into a cell significantly changes the environment inside of the cell and may terminate the cell life after the measurement. In contrast, when the T-probe is used, the ionization solvent is mixed with cellular compounds at the T-junction, outside of the cell, which minimizes the perturbation of the intracellular environment, potentially enabling time-dependent measurement of single living cells. Additionally, the T-probe has the advantage of longer time for MS data acquisition. The MS signal obtained from the dual bore single-probe can last only for about 15-30 seconds for one cell analysis, which may not leave enough time to perform more detailed MS analysis such as MS-MS. In contrast, the T-probe may provide much longer time for single-cell analysis (e.g., about 3-5 minutes per cell) potentially resulting in sufficient time to conduct a more detailed MS analysis for identifying species of interest.

Example 14

Figure 26A:
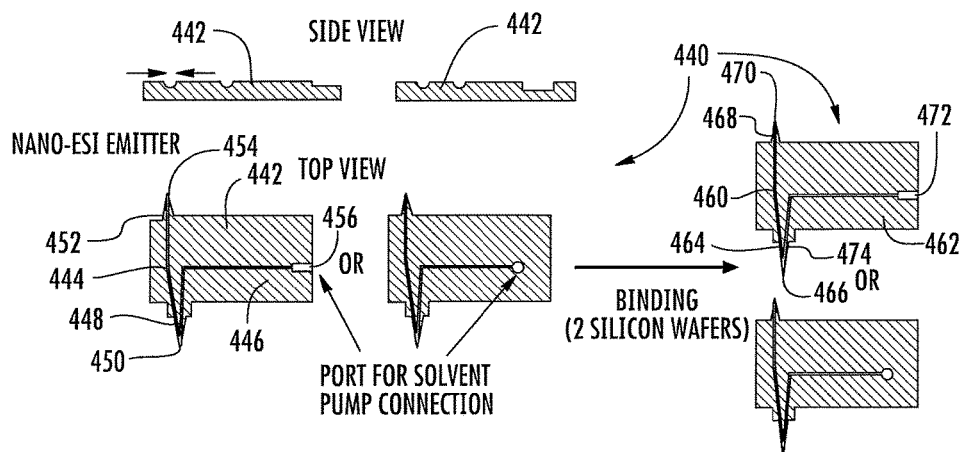
FIG. 26(a) depicts an alternate Single-probe configuration constructed using a silicon wafer.
Figure 26B:
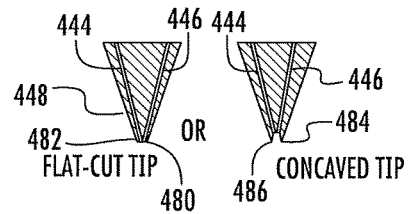
FIG. 26(b) depicts alternative sampling tips of the Single-probe configuration of FIG. 26(a).
Figure 26C:
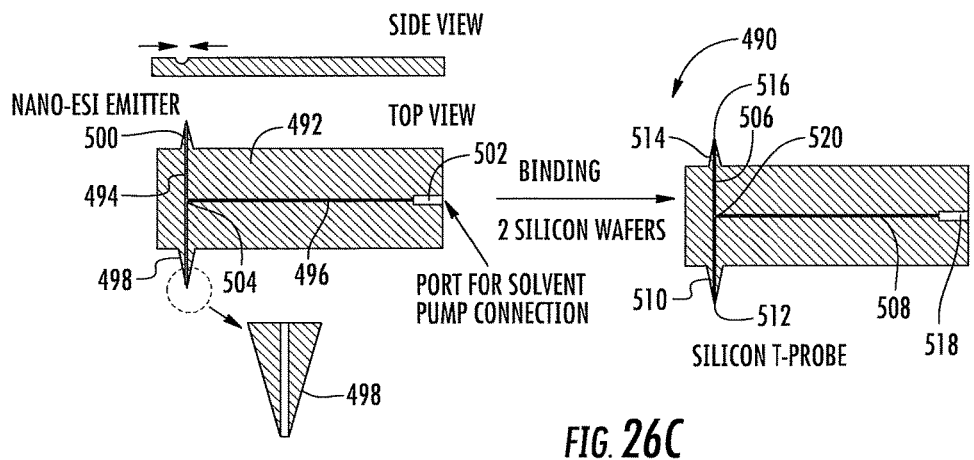
FIG. 26(c) depicts an alternate T-probe configuration constructed using a silicon wafer.

In another embodiment of the present disclosure, a hybrid T-probe designated by the reference numeral 440 in FIG. 26(*a*) is formed with "Single-probe-type" sampling tip. A sampling tip 448 having an opening 450 and an emitting tip 452 having an opening 454 are integrally formed in a complementary (top and bottom) pair of silicon wafers (a.k.a., substrates or chips) 442 (FIG. 26(*a*) showing only one silicon wafer 442). To fabricate the silicon wafer hybrid T-probe 440, a pair of complementary grooves, a sampling groove 444 and and a solvent-supplying groove 446, are formed in the wafer 442 which lead into the sampling tip 448. Openings 450 and 454 are in fluid communication via groove 444. As noted, the groove 444 in each wafer 442 extends from the sampling tip 448 to the emitting tip 452. Groove 446 extends from an inlet port 456 to the sampling tip 448, where it intersects, or nearly intersects with, the sampling groove 444 in the sampling tip 448 (see FIG. 26(*a*)). The widths of the grooves 444 and 446 may be in a range of, for example, about 1 μm to about 20 μm (e.g., about 5 μm to about 15 μm). The widths of the sampling tip 448 and emitting tip 452 may be in a range of, for example, about 2 μm to about 15 μm (e.g., about 5 μm to about 10 μm). The two complementary top and bottom wafers 442 are disposed upon each other so that the two complementary sampling grooves 444 form a sampling channel or a first channel 460 (sampling conduit or capillary) and the two solvent supplying grooves 446 form a solvent-supplying channel or a second channel 462 (sampling conduit or capillary). The two sampling tips 448 form a first tapered tip 464 having an opening 466 and the two emitting tips 452 form a second tapered tip 468 having an opening 470. The first channel 460 extends from the first tapered tip opening 466 to the second tapered tip opening 470. The second channel 462 extends from an inlet port 472 to a junction 474 with the first channel 460. The junction 474 of the first channel 460 and the second channel 462 is in the first tapered tip 464.

In an alternate embodiment, only one of the wafers is etched with the pair of grooves and the second wafer is flat. In an alternate embodiment, one of the wafers is etched with both the sampling groove and the solvent-supplying groove and the second wafer is etched with either the sampling groove or the solvent-supplying groove. The top and bottom wafers are connected by heat fusion, cohesions, or by an adhesive material to produce a silicon chip-based Single-probe with an integrated sampling tip, nano-ESI emitter, and solvent inlet. The solvent-providing capillary is optional because the solvent may be able to flow through wider grooves (e.g., 5 mm) that have been etched on the silicon wafer and that have been connected, via a port, to the solvent pump. The probe may be constructed with additional channels/conduits, for example three, four or more channels/conduits to form multibore probes as discussed elsewhere herein. In one embodiment, the sampling channel and the solvent-supplying channel each extend to the end of the sampling tip. Referring to FIG. 26(*b*), in one embodiment, the sampling tip 448 has a straight edge 480 (flat-cut tip) such that intersection 482 (junction) of the two channels is outside of the sampling tip 448. In an alternate embodiment, the sampling tip 448 has a concave or "scooped" tip 484 such that intersection (junction) of the two channels is in a "well" 486 inside the end of the sampling tip 448. The concave tip may enable the liquid junction to be more stably sustained, resulting in better sampling stability for MSI measurements. Either or both of the top and bottom silicon wafers may comprise internal or external electrically conductive filaments, coatings, ridges, or coated channels for conducting an electrical current for heating the contents of the probe as it passes through the sampling channel and/or the solvent supplying channel.

Example 15

In another embodiment of the present disclosure, a T-probe 490 is integrally formed in a silicon wafer (substrate or chip) 492 (FIG. 26(*c*). To fabricate a silicon wafer T-probe 490, a pair of complementary grooves 494 and 496 and sharp tips 498 and 500 are etched into two silicon wafers 492 (top and bottom) (FIG. 26(*c*) showing only one silicon wafer). A sampling groove 494 in each wafer 492 extends from a sampling tip 498 to an emitting tip 500. A solvent supplying groove 496 in each wafer 492 extends from an inlet port 502 to the sampling groove 494 where it forms a perpendicular intersection or an intersection 504 at a position between the sampling tip 498 and the emitting tip 500.

The widths of the grooves 494 and 496 may be in a range of, for example, about 1 µm to about 20 µm (e.g., about 5 µm to about 15 µm). The outer diameter of the sampling tip 498 may be in a range of, for example, about 2 µm to about 8 µm (e.g., about 2 µm to about 5 µm). The inner diameter of the sampling tip 498 may be in a range of, for example, about 1 µm to about 3 µm (e.g., about 2 µm). The two complementary top and bottom wafers 492 are disposed upon each other so that the two sampling grooves 494 form a sampling or a first channel 506 (sampling conduit or capillary) and the two solvent supplying grooves 496 form a solvent-supplying or second channel 508 (sampling conduit or capillary). The two sampling tips 498 form a first tapered tip 510 having an opening 512 and the two emitting tips 500 form a second tapered tip 514 having an opening 516. The first channel 506 extends from the first tapered tip opening 512 to the second tapered tip opening 516. The second channel 508 extends from an inlet port 518 to a junction 520 with the first channel 506. The junction 520 of the first channel 506 and the second channel 508 is at a position between the first tapered tip 510 and the second tapered tip 514.

In an alternate embodiment, only one of the wafers is etched with the pair of grooves and the second wafer is flat. In an alternate embodiment, one of the wafers is etched with both the sampling groove and the solvent-supplying groove and the second wafer is etched with either the sampling groove or the solvent-supplying groove. The top and bottom wafers are connected by heat fusion, cohesions, or by an adhesive material to produce a silicon chip-based T-probe with an integrated sampling tip, nano-ESI emitter, and solvent inlet. The solvent-providing capillary is optional because the solvent may be able to flow through wider grooves (e.g., 5 mm) that have been etched on the silicon wafer and that have been connected, via a port, to the solvent pump. The probe may be constructed with additional channels/conduits, for example three, four or more channels/conduits to form multibore probes as discussed elsewhere herein. In one embodiment, the sampling channel extends to the end of the sampling tip. Either or both of the top and bottom silicon wafers may comprise internal or external electrically conductive filaments, coatings, ridges, or coated channels for conducting an electrical current for heating the contents of the probe as it passes through the sampling channel and/or the solvent supplying channel. In the silicon chip-based T-Probe the sampled species from a cell is mixed with the solvent at the junction of the sampling channel and the solvent-supplying channel (not at the sampling tip). The nano-ESI provides the driving force to draw the sampled analytes from the sampling tip towards the nano-ESI emitter for ionization. Due to the semi-conductivity of silicon, the ionization voltage can be directly applied to the silicon chip and transmitted to the nano-ESI emitter.

Figure 27A:
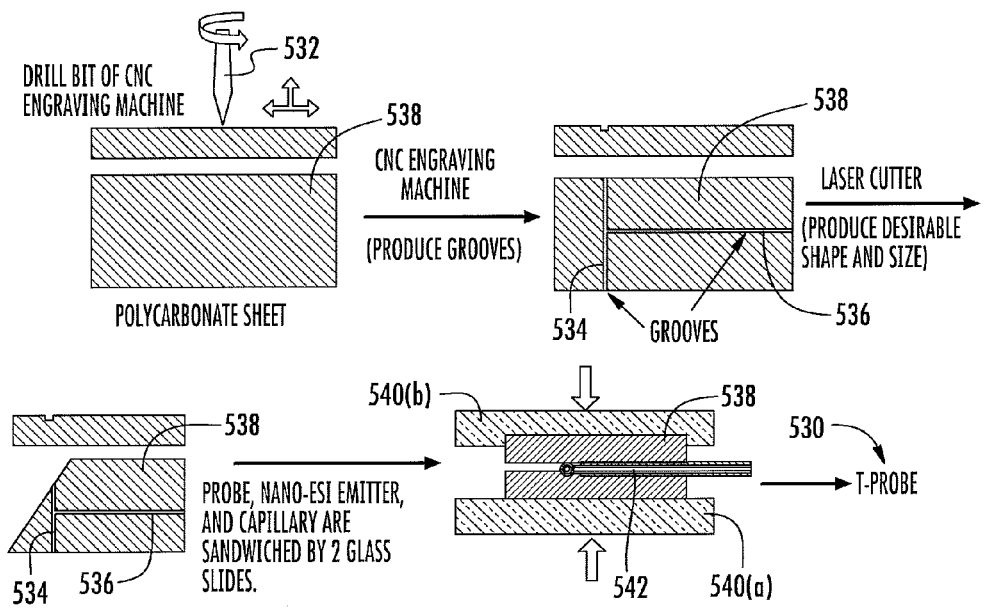
FIG. 27(a) depicts an alternate T-probe configuration.
Figure 27B:
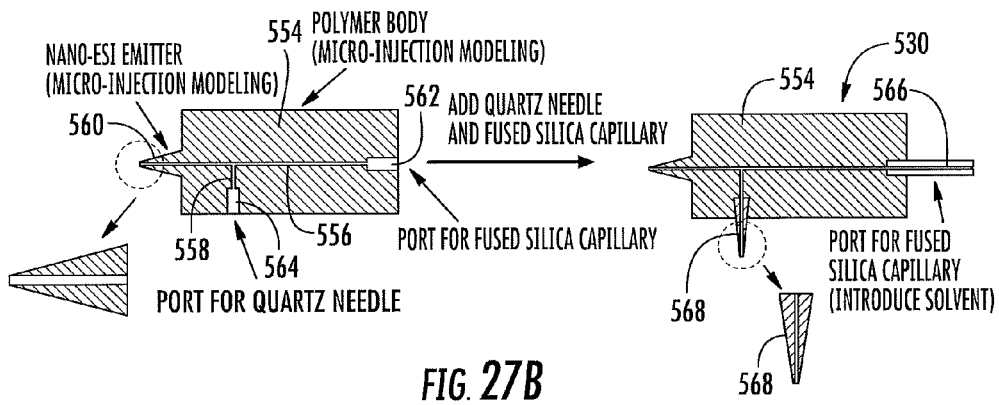
FIG. 27(b) depicts an alternative T-probe configuration.

Referring to FIGS. 27(a) and 27(b), shown therein is an alternative embodiment of a T-probe 530. Instruments which may be used in the fabrication of the T-probes of this embodiment include but are not limited to a CNC (Computer Numerical Control) Micro Engraver [CNC 3020, LiYang (LY) Welding Equipment Co., Ltd, Shenzhen, China)] and a precise laser cutter [LY3020 40W $CO_2$ Laser Engraving Cutting Machine Engraver Cutter, LiYang (LY) Welding Equipment Co., Ltd, Shenzhen, China]. The drill bit 532 of the micro-engraver is used to produce grooves 534 and 536 on plastic slides or a polycarbonate sheet 538. The drill bit 532 mounted on the CNC micro-engraver can be selected from different sizes, for example, but not limited to, OD ranges from 1 µm to 1 mm, to produce grooves 534 and 536 with different IDs. The laser cutter (not shown) is used to cut the slides 538 to produce a desirable shape and size before fabrication (FIG. 27(a)). The produced slides 538 with grooves 534 and 536 are fabricated into the T-probe 530 in a similar way as described previously for the embodiment shown in FIG. 25(b) [i.e., using an oven] to fuse the sandwiched glass slides 540(a) and 540(b), plastic slide 538, and capillaries 542 into the T-probe 530. Because both instruments can be programmed for batch processing, the plastic slides can be produced with significantly improved reproducibility and productivity.

The micro-injection modeling technique is used to precisely produce the T-probe bodies 554, which are used to assemble T-probe 530 in mass production. The T-probe body 554 can be made from materials (such as, but not limited to, PEEK, polycarbonate, and polystyrene) that are chemically stable in common mass spectrometry solvents (e.g., water, methanol, and acetonitrile). Using the micro-injection modeling technique, the polymer materials will be melted and squeezed into a desired model to produce a T-probe body 554 (FIG. 27(b)). Each T-probe body 554 contains a first groove 556 and a second groove 558, a preformed nano-ESI emitter tip 560 (for MS ionization), a port 562 for receiving a fused silica capillary 566 (for solvent introduction), and a port 564 for receiving a sharp quartz needle 568 (for single cell insertion and/or probing). In at least one alternative embodiment, the T-probe body 554 can be produced from precise machining (i.e., cutting, milling, and drilling) of the corresponding polymer material; however, the productivity of the mass production is expected to be lower than the micro-injection modeling.

In at least one embodiment, as shown in FIG. 27(b), the T-probe 530 can be fabricated by inserting the fused silica capillary 566 into the port 562 and the quartz needle 568 into the port 564 in the T-probe body 554. According to the IDs of ports 562 and 564 in the T-probe body 554, the solvent-providing capillary 566 (and quartz needle 568) can be selected (and prepared) from commercial products with a variety of ODs (such as, but not limited to, 90, 110, 150, and 360 µm) and IDs (such as, but not limited to, 5, 10, 50, 75, 100, and 150 µm). The quartz needle 568 can be pulled from the fused silica capillaries using a programmable laser puller, and tip size can be selected within a broad range (such as, but not limited to, OD: 1-10 µm and ID: 0.5-8 µm). The T-probe body 554 can be reused, whereas both fused silica capillary 566 and quartz needle 568 can be replaced as needed, for example if they become dull or are broken. The nano-ESI emitter 560 can be directly formed through the micro-injection modeling, and it is expected to have stable performance and long life-time. Depending on the design of the model for micro-injection process, the tip size of the nano-ESI emitter 560 can be formed with different ODs (such as, but not limited to, 1-30 µm) and IDs (such as, but not limited to, 0.5-20 µm).

As described herein in various embodiments, in use, a cell or tissue source is sampled. The sample is obtained from the cell or tissue source via a sample analysis system. The system includes a sampling probe. The sampling probe can include a polymeric substrate and/or a silicon substrate. The polymeric substrate has a first bore and a second bore which intersect at a junction. The first bore has a first tapered capillary tip extending from a first end thereof, and a second tapered capillary tip extending from a second end thereof, wherein the junction is at a position between the first tapered capillary tip and the second tapered capillary tip such that a solvent introduced into the second bore flows through the junction into the first bore. The silicon substrate has a first channel, a second channel, a first tapered tip with an opening, and a second tapered tip with an opening. The first channel extends from the first tapered tip opening to the second tapered tip opening, and wherein the second channel extends from an inlet port to a junction with the first channel.

It will be understood from the foregoing description that various modifications and changes may be made in the various embodiments of the present disclosure without departing from their true spirit. For example, active regions and injection regions of the lasers can be constructed in a variety of manners and with various materials, and thicknesses of materials and layers. The description provided herein is intended for purposes of illustration only and is not intended to be construed in a limiting sense. Thus, while the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the presently disclosed inventive concepts.

What is claimed is:

1. A sampling probe, comprising:
a polymeric substrate having a first bore and a second bore which intersect substantially perpendicular at a junction, the first bore having a first tapered capillary tip extending from a first end thereof, and a second tapered capillary tip extending from a second end thereof, wherein the junction is at a position between the first tapered capillary tip and the second tapered capillary tip such that a solvent introduced into the second bore flows through the junction into the first bore.

2. The sampling probe of claim 1, wherein the polymeric substrate is constructed of a pair of flat polymeric sheets bonded together.

3. The sampling probe of claim 1 in fluid communication with a mass spectrometer via the second tapered capillary tip, and in fluid communication with a solvent source via the second bore, forming a sample analysis system.

4. A sampling probe, comprising: a silicon substrate having a first channel, a second channel, a first tapered tip with an opening, and a second tapered tip with an opening, wherein the first channel extends from the first tapered tip opening to the second tapered tip opening, and wherein the second channel extends substantially perpendicular from an inlet port to a junction with the first channel.

5. The sampling probe of claim 4, wherein the junction of the first channel and the second channel is in the first tapered tip.

6. The sampling probe of claim 4, wherein the junction of the first channel and the second channel is at a position between the first tapered tip and the second tapered tip.

7. The sampling probe of claim 4, wherein the silicon substrate is constructed of a pair of flat silicon sheets bonded together.

8. The sampling probe of claim 4 in fluid communication with a mass spectrometer via the second tapered tip, and in fluid communication with a solvent source via the second channel, forming a sample analysis system.

9. A method of sampling a cell or tissue source, comprising: obtaining a sample from the cell or tissue source via a sample analysis system comprising a sampling probe, wherein the sampling probe comprises:
(1) a polymeric substrate having a first bore and a second bore which intersect substantially perpendicular at a junction, the first bore having a first tapered capillary tip extending from a first end thereof, and a second tapered capillary tip extending from a second end thereof, wherein the junction is at a position between the first tapered capillary tip and the second tapered capillary tip such that a solvent introduced into the second bore flows through the junction into the first bore; and/or
(2) a silicon substrate having a first channel, a second channel, a first tapered tip with an opening, and a second tapered tip with an opening, wherein the first channel extends from the first tapered tip opening to the second tapered tip opening, and wherein the second channel extends from an inlet port to a junction with the first channel.

* * * * *